US010618932B2

(12) United States Patent
LaBaer

(10) Patent No.: US 10,618,932 B2
(45) Date of Patent: Apr. 14, 2020

(54) METHOD FOR TARGETED PROTEIN QUANTIFICATION BY BAR-CODING AFFINITY REAGENT WITH UNIQUE DNA SEQUENCES

(71) Applicant: ARIZONA BOARD OF REGENTS ON BEHALF OF ARIZONA STATE UNIVERSITY, Scottsdale, AZ (US)

(72) Inventor: Joshua LaBaer, Chandler, AZ (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 0 days.

(21) Appl. No.: 16/480,601

(22) PCT Filed: Feb. 21, 2018

(86) PCT No.: PCT/US2018/018908
§ 371 (c)(1),
(2) Date: Jul. 24, 2019

(87) PCT Pub. No.: WO2018/156553
PCT Pub. Date: Aug. 30, 2018

(65) Prior Publication Data
US 2019/0366237 A1 Dec. 5, 2019

Related U.S. Application Data

(60) Provisional application No. 62/461,681, filed on Feb. 21, 2017.

(51) Int. Cl.
C07H 21/04 (2006.01)
B01D 15/38 (2006.01)
G01N 33/68 (2006.01)

(52) U.S. Cl.
CPC ......... *C07H 21/04* (2013.01); *B01D 15/3819* (2013.01); *G01N 33/6803* (2013.01); *G01N 33/6854* (2013.01); *G01N 2458/10* (2013.01)

(58) Field of Classification Search
CPC ..................................................... C07H 21/04
See application file for complete search history.

(56) References Cited

U.S. PATENT DOCUMENTS 9,442,111 B2  9/2016  Lindsay
9,535,070 B2  1/2017  Saul
(Continued)

FOREIGN PATENT DOCUMENTS

WO  2003073987 A2  9/2003
WO  2012021887 A2  2/2012
(Continued)

OTHER PUBLICATIONS

International Searching Authority, International Search Report and Written Opinion for application PCT/US2018/018908, dated Jul. 9, 2018.
Yang, et al. Genetically encoded protein photocrosslinker with a transferable mass spectrometry-identifiable label. Nat Commun. Jul. 27, 2016, vol. 7, p. 12299; Abstract.
(Continued)

*Primary Examiner* — Jeremy C Flinders
(74) *Attorney, Agent, or Firm* — Quarles & Brady LLP; Jessica L. Lewis

(57) ABSTRACT

Provided herein are affinity reagents having affinity for particular target, each reagent having a unique DNA barcode, and methods for using the same to measure the abundance of targets in a sample. In particular, methods are provided in which unique barcodes linked to affinity reagents are contacted to a sample to bind antigens if present in said sample. In cases in which the affinity reagents are antibodies and the targets are antigens, antibodies that are bound to their target antigens can be separated from unbound antibodies and the DNA barcode associated with (Continued)

the affinity reagent is amplified, such as with a PCR reaction. In some cases, amplified barcode DNA is subjected to DNA sequencing as a measure of the levels of the target protein in the sample.

1 Claim, 4 Drawing Sheets

Specification includes a Sequence Listing.

(56) References Cited

U.S. PATENT DOCUMENTS

| | | | |
|---|---|---|---|
| 9,719,144 | B2 | 8/2017 | Krajmalnik-Brown |
| 9,857,374 | B2 | 1/2018 | Labaer |
| 9,938,523 | B2 | 4/2018 | Labaer |
| 10,045,990 | B2 | 8/2018 | Festa |
| 10,351,842 | B2 | 7/2019 | LaBaer |
| 2014/0161721 | A1 | 6/2014 | Hatchwell et al. |
| 2014/0162902 | A1 | 6/2014 | Labaer |
| 2014/0371091 | A1 | 12/2014 | Wiktor |
| 2015/0362497 | A1 | 12/2015 | Anderson |
| 2016/0041159 | A1 | 2/2016 | Labaer |
| 2016/0122751 | A1 | 5/2016 | LaBaer |
| 2016/0195546 | A1 | 7/2016 | Labaer |
| 2017/0045515 | A1 | 2/2017 | Anderson |
| 2017/0115299 | A1 | 4/2017 | Saul |
| 2017/0176423 | A1 | 6/2017 | Anderson |
| 2017/0356029 | A1 | 12/2017 | Krajmalnik-Brown |
| 2017/0363631 | A1 | 12/2017 | Labaer |
| 2018/0067117 | A1 | 3/2018 | Labaer |
| 2018/0201923 | A1 | 7/2018 | Labaer |
| 2018/0224448 | A1 | 8/2018 | Wang |
| 2018/0267029 | A1 | 9/2018 | Wiktor |
| 2018/0320230 | A1 | 11/2018 | Labaer |
| 2019/0004051 | A1 | 1/2019 | Labaer |
| 2019/0062728 | A1 | 2/2019 | Labaer |
| 2019/0127778 | A1 | 5/2019 | Labaer |
| 2019/0144923 | A1 | 5/2019 | Krajmalnik-Brown |
| 2019/0162725 | A1 | 5/2019 | Magee |
| 2019/0302122 | A1 | 10/2019 | Katchman |

FOREIGN PATENT DOCUMENTS

| | | | |
|---|---|---|---|
| WO | 2013019680 | A1 | 2/2013 |
| WO | 2013063126 | A2 | 5/2013 |
| WO | 2013090364 | A1 | 6/2013 |
| WO | 2013176774 | A1 | 11/2013 |
| WO | 2013176774 | A9 | 11/2013 |
| WO | 2014120902 | A1 | 8/2014 |
| WO | 2014143954 | A2 | 9/2014 |
| WO | 2014145458 | A1 | 9/2014 |
| WO | 2015148202 | A1 | 10/2015 |
| WO | 2015167678 | A1 | 11/2015 |
| WO | 2015167678 | A8 | 11/2015 |
| WO | 2015175755 | A1 | 11/2015 |
| WO | 2016094558 | A1 | 6/2016 |
| WO | 2016141044 | A1 | 9/2016 |
| WO | 2017048709 | A1 | 3/2017 |
| WO | 2017075141 | A1 | 5/2017 |
| WO | 2017075141 | A8 | 5/2017 |
| WO | 2017123648 | A1 | 7/2017 |
| WO | 2017218677 | A2 | 12/2017 |
| WO | 2018013531 | A1 | 1/2018 |
| WO | 2018013531 | A8 | 1/2018 |
| WO | 2019136169 | A1 | 7/2019 |

OTHER PUBLICATIONS

Ramachandran, N. et al. Next-generation high- density self-assembling functional protein arrays. Nat. Methods 2008, 5 (6), 535-8.
Ramachandran, N. et al. Self-assembling protein microarrays. Science 2004, 305 (5680), 86-90.
Ramachandran, N. et al. Tracking humoral responses using self assembling protein microarrays. Proteomics Clin. Appl. 2008, 2 (10-11), 1518-27.
Richardson, A. L. et al. X chromosomal abnormalities in basal-like human breast cancer. Cancer Cell 2006, 9 (2), 121-32.
Robinson, W. H. et al. Autoantigen microarrays for multiplex characterization of autoantibody responses. Nat. Med. 2002, 8 (3), 295-301.
Schmoor, C. et al. Long-term prognosis of breast cancer patients with 10 or more positive lymph nodes treated with CMF. Eur. J. Cancer 2001, 37 (9), 1123-31.
Sioud, M. et al. Profiling the immune response in patients with breast cancer by phage-displayed cDNA libraries. Eur. J. lmmunol. 2001, 31 (3), 716-25.
Stockert, E. et al. A survey of the humoral immune response of cancer patients to a panel of human tumor antigens. J. Exp. Med. 1998, 187 (8), 1349-54.
Stoll, D. et al. Protein microarray technology. Front. Biosci. 2002, 7, c13-32.
Storey, J. A direct approach to false discovery rates. J. R. Stat. Soc. B 2002, 64 (3), 479-98.
Tamimi, R. M. et al. Endogenous hormone levels, mammographic density, and subsequent risk of breast cancer in postmenopausal women. J. Natl. Cancer Inst. 2007, 99 (15), 1178-87.
Tamimi, R. M. et al. Endogenous sex hormone levels and mammographic density among postmenopausal women. Cancer Epidemiol. Biomarkers Prev. 2005, 14 (11 Pt 1), 2641-7.
Templin, M. F. et al. Protein microarrays: promising tools for proteomic research. Proteomics 2003, 3 (11), 2155-66.
Torres, V. A. et al. Rab5 mediates caspase-8-promoted cell motility and metastasis. 2010. Mol. Biol. Cell , 21 (2), 369-76.
Tozlu, S. et al. Identification of novel genes that co-cluster with estrogen receptor alpha in breast tumor biopsy specimens, using a large-scale real-time reverse transcription-PCR approach. Endocr.-Relat. cancer 2006, 13 (4), 1109-20.
Wandall, H. H. et al. Cancer biomarkers defined by autoantibody signatures to aberrant O- glycopeptide epitopes. 2010. Cancer Res., 70 (4), 1306-13.
Wang, C. C. et al. Glycan microarray of Globo H and related structures for quantitative analysis of breast cancer. Proc. Natl. Acad. Sci. U.S.A. 2008, 105 (33), 11661-6.
Wang, X. et al. Autoantibody signatures in prostate cancer. N. Engl. J. Med. 2005, 353 (12), 1224-35.
Witt, A. E. et al. Functional proteomics approach to investigate the biological activities of cDNAs impli- cated in breast cancer. J. Proteome Res. 2006, 5 (3), 599-610.
Wong, J. et al. Rapid detection of antibodies in sera using multiplexed self-assembling bead arrays. J. Immunol. Methods 2009, 350 (1-2), 171-82.
Wulfkuhle, J. et al, New approaches to proteomic analysis of breast cancer. Proteomics 2001, 1 (10), 1205-15.
Zhao, H. et al. Different gene expression patterns in invasive lobular and ductal carcinomas of the breast. Mol. Biol. Cell 2004, 15 (6), 2523-36.
Zhou, J. et al. A novel gene, NMES1, downregulated in human esophageal squamous cell carcinoma. Int. J. Cancer 2002, 101 (4), 311-6.
Zhu, H. et al. Global analysis of protein activities using proteome chips. Science 2001, 293 (5537), 2101-5.
U.S. Appl. No. 16/097,791.
Anderson, K. S. et al. Application of protein microarrays for multiplexed detection of antibodies to tumor antigens in breast cancer. J. Proteome Res. 2008, 7 (4), 1490-9.
Anderson, K. S. et al. In Using custom protein microarrays to identify autoantibody biomarkers for the early detection of breast cancer; San Antonio Breast Cancer Symposium, San Antonio, TX, 2008.
Anderson, K. S. et al. The sentinel within: exploiting the immune system for cancer biomarkers. J. Proteome Res. 2005, 4 (4), 1123-33.
Anderson, N. L. et al. The human plasma proteome: history, character, and diagnostic prospects. Mol. Cell. Proteomics 2002, 1 (11), 845-67.

(56) References Cited

OTHER PUBLICATIONS

Baugher, P. J. et al. Rac1 and Rac3 isoform activation is involved in the invasive and metastatic phenotype of human breast cancer cells. Breast Cancer Res. 2005, 7 (6), R965-74.

Bouwman, K. et al. Microarrays of tumor cell derived proteins uncover a distinct pattern of prostate cancer serum immunoreactivity. Proteomics 2003, 3 (11), 2200-7.

Breiman, L. Random Forests. Mach. Learn. 2001, 45 (1), 5-32.

Chapman, C. et al. Autoantibodies in breast cancer: their use as an aid to early diagnosis. Ann. Oncol. 2007, 18 (5), 868-73.

Chatterjee, M. et al. Diagnostic markers of ovarian cancer by high-throughput antigen cloning and detection on arrays. Cancer Res. 2006, 66 (2), 1181-90.

Chen, G. et al. Autoantibody profiles reveal ubiquilin 1 as a humoral immune response target in lung adenocarcinoma. Cancer Res. 2007, 67 (7), 3461-7.

Chen, K. Y. et al. The role of tyrosine kinase Etk/Bmx in EGF-induced apoptosis of MDA- MB-468 breast cancer cells. Oncogene 2004, 23 (10), 1854-62.

Chen, Y. et al. The molecular mechanism governing the oncogenic potential of SOX2 in breast cancer. J. Biol. Chem. 2008, 283 (26), 17969-78.

Csepregi, A. et al. Characterization of a lipoyl domain-independent B-cell autoepitope on the human branched-chain acyltransferase in primary biliary cirrhosis and overlap syndrome with autoim- mune hepatitis. Clin. Dev. Immunol. 2003, 10 (2-4), 173-81.

Desmetz, C. et al. Identification of a new panel of serum autoantibodies associated with the presence of in situ carcinoma of the breast in younger women. Clin. Cancer Res. 2009, 15 (14), 4733-41.

Edwards, B. K. et al. Annual report to the nation on the status of cancer, 1975-2002, featuring population-based trends in cancer treatment. J. Natl. Cancer Inst. 2005, 97 (19), 1407-27.

Efron, B. Bootstrap Methods: Another Look at the Jackknife. Ann. Stat. 1979, 7, 1-26.

Esserman, L. et al. Rethinking screening for breast cancer and prostate cancer. J. Am. Med. Assoc. 2009, 302 (15), 1685-92.

Esserman, L. J. et al. A role for biomarkers in the screening and diagnosis of breast cancer in younger women. Expert Rev. Mol. Diagn. 2007, 7 (5), 533-44.

Forti, S. et al. Identification of breast cancer-restricted antigens by antibody screening of SKBR3 cDNA library using a preselected patient's serum. Breast Cancer Res. Treat. 2002, 73 (3), 245-56.

Fossa, A. et al. Serological cloning of cancer/testis antigens expressed in prostate cancer using cDNA phage surface display. Cancer Immunol. Immunother. 2004, 53 (5), 431-8.

Gnjatic, S. et al. Seromic profiling of ovarian and pancreatic cancer. Proc. Natl. Acad. Sci. U.S.A. 2010.

Grzmil, M. et al. An oncogenic role of elF3e/INT6 in human breast cancer. 2010. Oncogene, 29 (28), 4080-9.

Gure, A. O. et al. Human lung cancer antigens recognized by autologous antibodies: definition of a novel cDNA derived from the tumor suppressor gene loc us on chromosome 3p21.3. Cancer Res. 1998, 58 (5), 1034-41.

Gure, A. O. et al. Serological identification of embryonic neural proteins as highly immunogenic tumor antigens in small cell lung cancer. Proc. Natl. Acad. Sci. U.S.A. 2000, 97 (8), 4198-203.

Harris, L. et al. American Society of Clinical Oncology 2007 update of recommendations for the use of tumor markers in breast cancer. J. Clin. Oncol. 2007, 25 (33), 5287-312.

Hartmann, L. C. et al. Benign breast disease and the risk of breast cancer. N. Engl. J. Med. 2005, 353 (3), 229-37.

Hattori, T. et al. Rheumatoid arthritis-related antigen 47 kDa (RA-A47) is a product of colligin-2 and acts as a human HSP47. J. Bone Miner. Metab. 2000, 18 (6), 328-34.

Hodi, F. S. et al. ATP6S1 elicits potent humoral responses associated with immune—mediated tumor destruction. Proc. Natl. Acad. Sci. U.S.A. 2002, 99 (10), 6919-24.

Hudson, M. E. et al. Identification of differentially expressed proteins in ovarian cancer using high-density protein microarrays. Proc. Natl. Acad. Sci. U.S.A. 2007, 104 (44), 17494-9.

Huttenhower, C. et al. Exploring the human genome with functional maps. Genome Res. 2009, 19 (6), 1093-106.

Iejima, D. et al. FRS2beta, a potential prognostic gene for non-small cell lung cancer, encodes a feedback inhibitor of EGF receptor family members by ERK binding. 2010. Oncogene, 29 (21), 3087-99.

Jager, D. et al. Antibodies and vaccines—hope or illusion. Breast (Edinburgh, Scotland) 2005, 14 (6), 631-5.

Jager, D. et al. Identification of a tissue-specific putative transcription factor in breast tissue by serological screen-ing of a breast cancer library. Cancer Res. 2001, 61 (5), 2055-61.

Jager, D. et al. Identification of tumor—restricted antigens NY-BR-1, SCP-1, and a new cancer/testis-like antigen NW-BR-3 by serological screening of a testicular library with breast cancer serum. Cancer Immun. 2002, 2, 5.

Joos, T. O. et al. Miniaturised multiplexed immunoassays. Curr. Opin. Chem. Biol. 2002, 6 (1), 76-80.

Kano, S. et al. Tripartite motif protein 32 facilitates cell growth and migration via degradation of Abl-interactor 2. Cancer Res. 2008, 68 (14), 5572-80.

Koziol, J. A. et al. Recursive partitioning as an approach to selection of immune markers for tumor diagnosis. Clin. Cancer Res. 2003, 9 (14), 5120-6.

Kwok, S. et al. Transforming growth factor—beta1 regulation of ATF-3 and identification of ATF-3 target genes in breast cancer cells. J. Cell. Biochem. 2009, 108 (2), 408-14.

Lichtenfels, R. et al. Identification of metabolic enzymes in renal cell carcinoma utilizing PROTEOMEX analyses. Biochim. Biophys. Acta 2003, 1646 (1-2), 21-31.

Macbeath, G. et al. Printing proteins as microarrays for high-throughput function determination. Science 2000, 289 (5485), 1760-3.

Mahul-Mellier, A. L. et al. Alix and ALG-2 are involved in tumor necrosis factor receptor 1-induced cell death. J. Biol. Chem. 2008, 283 (50), 34954-65.

Marchese, R. D. et al. Optimization and validation of a multiplex, electrochemilumines- cence-based detection assay for the quantitation of immunoglo- bulin G serotype-specific antipneumococcal antibodies in human serum. Clin. Vaccine Immunol. 2009, 16 (3), 387-96.

Mcclish, D. K. Analyzing a portion of the ROC curve. Med. Decis. Making 1989, 9 (3), 190-5.

Minenkova, O. et al. Identification of tumor—associated antigens by screening phage-displayed human cDNA libraries with sera from tumor patients. Int. J. Cancer 2003, 106 (4), 534-44.

Mira, J. P. et al. Endogenous, hyperactive Rac3 controls proliferation of breast cancer cells by a p21-activated kinase-dependent pathway. Proc. Natl. Acad. Sci. U.S.A. 2000, 97 (1), 185-9.

Nese, N. et al. Comparison of the desmoplastic reaction and invading ability in invasive ductal carcinoma of the breast and prostatic adenocarcinoma based on the expression of heat shock protein 47 and fascin. 2010. Anal. Quant. Cytol. Histol., 32 (2), 90-101.

Palijan, A. et al. Ligand-dependent corepressor LCoR is an attenuator of progesterone-regulated gene expression. J. Biol. Chem. 2009, 284 (44), 30275-87.

Parkin, D. M. et al. Global cancer statistics, 2002. CA Cancer J. Clin. 2005, 55 (2), 74-108.

Petricoin, E. et al. Clinical proteomics: revolutionizing disease detection and patient tailoring therapy. J. Proteome Res. 2004, 3 (2), 209-17.

Qiu, J. et al. Development of natural protein microarrays for diagnosing cancer based on an antibody response to tumor antigens. J. Proteome Res. 2004, 3 (2), 261-7.

Qian et al., Identification of Digital Differential Expression Patterns of a Novel Human Gene (UBAP1) by an Expressed Sequence Tag Strategy. Chinese Journal of Cancer, 2002, 21(3): 225-228. Abstract only.

METHOD FOR TARGETED PROTEIN QUANTIFICATION BY BAR-CODING AFFINITY REAGENT WITH UNIQUE DNA SEQUENCES

CROSS-REFERENCE TO RELATED APPLICATIONS

This application represents the national stage entry of PCT International Application No. PCT/US2018/018908, filed on Feb. 21, 2018, and claims the benefit of U.S. Application Ser. No. 62/461,681, filed on Feb. 21, 2017, each of which is incorporated by reference herein as if set forth in its entirety.

STATEMENT REGARDING FEDERALLY SPONSORED RESEARCH OR DEVELOPMENT

Not applicable.

BACKGROUND

With the advent of various 'omics' technologies and methods which stratify samples and diseases based on measuring many variables simultaneously, there is an increasing demand for high throughput tools that quantify specific targets. There are already numerous genomics tools that assess gene expression, gene copy number, mutations, etc. at a global scale to determine subtypes of disease that might be useful for prognostication and management of therapy. But it is well known that the genome (which is a blue print) does not always reflect the actual state of biology at any time and gene measurements are not always possible from readily accessible samples like blood. Thus, there is a strong desire to have similar high throughput tools to measure the proteome, which is the product of the genome and more closely reflects the current state of biology. However, high throughput measurement of the proteome is much more challenging than similar genome measurements, because there is no protein equivalent to the base pairing measurements that emerge from the inherent double-stranded nature of DNA.

There is a wide variety of methods to measure proteins. These can be generally divided into antibody-based methods and chemistry-based methods. By far, the most common chemistry-based method is mass spectrometry, which is most commonly employed by ionizing peptides (created by proteolytic digestion) and measuring their mobility in a magnetic field. The accuracy of these instruments is sufficient to identify virtually any protein by comparing its spectrum to spectrums predicted from the genome. Although nearly universal in its ability to detect proteins and even modified proteins, mass spectrometry is very low throughput. A thorough examination of single sample can take hours and it requires great care to run a set samples in a fashion that allows comparison of one run to the next. There are many other tools that detect proteins chemically, but they are not capable of identifying specific proteins in a universal manner.

Detection of proteins is most commonly accomplished with antibodies (or more generally, affinity reagents), and include many different configurations such as western blots, immunoprecipitation, flow cytometry, reverse phase protein arrays, enzyme linked immunosorbent assay (ELISA), and many others. These applications all rely on antibodies that recognize specific targets, and which can bind with extraordinary selectivity and affinity. There are currently more than 2,000,000 antibodies available on the market that target a large fraction of the human proteome. It is important to note that not all antibodies are high quality, but many are quite good and methods to produce antibodies have become routine. Although the use of an antibody to measure its target can be relatively fast, it is not straightforward to multiplex measurements using many antibodies simultaneously. Accordingly, there remains a need in the art for improved methods for simultaneous multiplexed detection and measurement of many proteins (including specific post-translational forms of proteins) or other target molecules.

SUMMARY

In a first aspect, provided herein is a composition comprising a plurality of modified affinity reagents, each affinity reagent of the plurality comprising a unique identifying nucleotide sequence relative to other affinity reagents of the plurality, wherein each identifying nucleotide sequence is flanked by a first amplifying nucleotide sequence and a second amplifying nucleotide sequence. Affinity reagents of the plurality can be antibodies. Affinity reagents of the plurality can be peptide aptamers or nucleic acid aptamers. An identifying nucleotide sequence can be attached to an affinity reagent by a linker comprising a cleavable protein photocrosslinker. An identifying nucleotide sequence can be attached to an affinity reagent by a linker comprising a fluorescent moiety. Unique identifying nucleotide sequences of the plurality can comprise one or more of SEQ ID Nos:104-203.

In another aspect, provided herein is a method for high throughput target molecule identification and quantification. The method can comprise or consist essentially of contacting a sample with a modified affinity reagent under conditions that promote binding of the modified affinity reagent to its target molecule if present in the contacted sample; removing unbound modified affinity reagent from the contacted sample; and amplifying and sequencing an identifying nucleotide sequence coupled to said modified affinity reagent whereby the target molecule is identified and quantified based on detection of the identifying nucleotide sequence. The method can further comprise adding a linker to an affinity reagent to form the modified affinity reagent, wherein the linker comprises the identifying nucleotide sequence flanked by a pair of amplifying nucleotide sequences. The affinity reagent can be an antibody. The adding step can further comprise adding a linker to a region of the antibody that is not an antigen binding region. The adding step can further comprise adding a linker to a fragment crystallizable region (Fc region) of the antibody. The affinity reagent can be an aptamer. The identifying nucleotide sequence can have a length of about 10 nucleotides to about 20 nucleotides. The identifying nucleotide sequence can have a length of about 12 nucleotides. The linker can be selected from SEQ ID Nos:104-203. The identifying nucleotide sequence can comprise SEQ ID NO:1 or a barcode sequence set forth in Table 1. The identifying nucleotide sequence can comprise about 50% of AT base pairs and about 50% of GC base pairs. The amplifying sequence can have a length ranging from 20 to 30 base pair. The amplifying sequence can comprise SEQ ID NO:2. The amplifying sequence can comprise SEQ ID NO:3. The linker can further comprise a fluorescent protein or a cleavable protein photocrosslinker.

In a further aspect, provided herein is a kit for high throughput protein quantification. The kit can comprise X modified affinity reagent(s), where X is equal to or greater than 1, each modified affinity reagent comprising a linker, where the linker comprising an identifying nucleotide sequence flanked by a pair of amplifying nucleotide sequences; and each modified affinity reagent comprising a different identifying nucleotide sequence from other modified affinity reagents. The linker can be selected from SEQ ID Nos:104-203.

BRIEF DESCRIPTION OF THE DRAWINGS

The present disclosure will be better understood and features, aspects, and advantages other than those set forth above will become apparent when consideration is given to the following detailed description thereof. Such detailed description makes reference to the following drawings, wherein.

DETAILED DESCRIPTION

Figure 1:
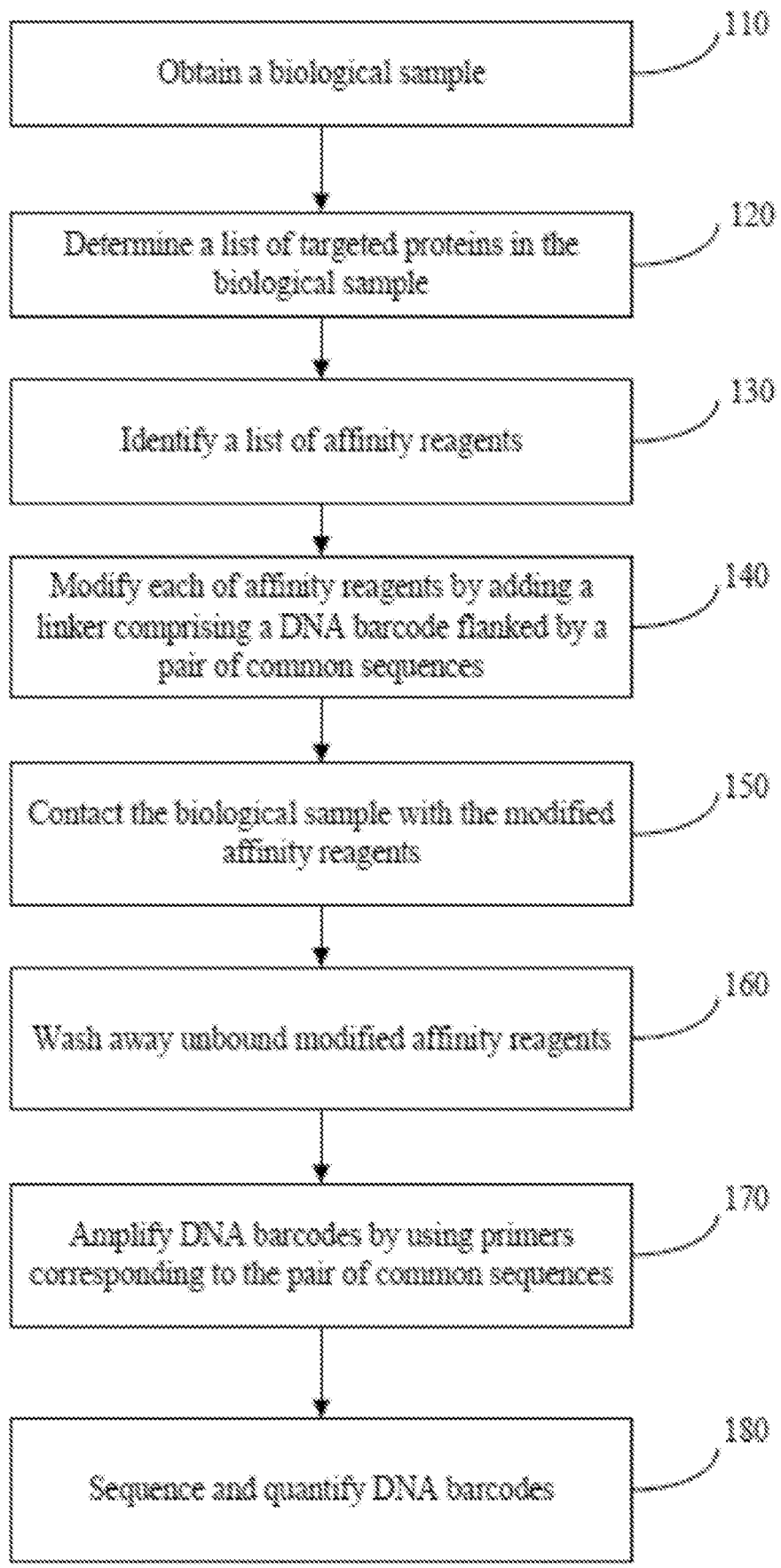
FIG. 1 is a flowchart that illustrates steps of a method for high throughput protein quantification.

The compositions and methods described herein couples the ability of antibodies (or virtually any affinity reagent) to recognize their targets with a unique DNA barcode that enables the detection of the antibody using, for example, next generation DNA sequencing methods. This disclosure is based at least in part on the inventor's development of a quantitative, multiplexed, bar-coded antigen library for detection and measurement of immune responses in pathogen-induced cancers including, for example, multiple serotypes of HPV (Human Papillomavirus)-positive Oropharyngeal carcinomas (OPC).

Affinity Reagents

Accordingly, in a first aspect, provided herein are affinity reagents having affinity for particular target molecules and comprising a unique DNA barcode, where the affinity reagent is useful to detect and measure the abundance of targets in a sample. Advantageously, a plurality of affinity reagents can be used to simultaneously measure a plurality of targets in a single sample. Accordingly, in some cases, affinity reagents of this disclosure are provided as a library of affinity reagents for multiplexed detection and measurement of multiple distinct targets in a single sample. As used herein, the term "affinity reagent" refers to an antibody, peptide, nucleic acid, or other small molecule that specifically binds to a biological molecule ("biomolecule") of interest in order to identify, track, capture, and/or influence its activity. In some embodiments, the affinity reagent is an antibody. In other embodiments, the affinity reagent is an aptamer.

In some cases, the affinity reagents are antibodies having specificity for particular protein (e.g., antigen) targets, where the antibodies are linked to a DNA barcode. In such cases, an antibody affinity reagent is contacted to a sample under conditions that promote binding of the affinity reagent to its target antigen when present in said sample. Antibodies that are bound to their target antigens can be separated from unbound antibodies by washing unbound reagents from the sample. In some embodiments, the DNA bar code associated with the affinity reagent is amplified, such as by polymerase chain reaction (PCR), and the amplified barcode DNA is subjected to DNA sequencing to provide a measure of target antigen in the contacted sample.

Any antibody can be used for the affinity reagents of this disclosure. Preferably, the antibodies bind tightly (i.e., have high affinity for) target antigens. It will be understood that antibodies selected for use in affinity reagents will vary according to the particular application. In some cases, the antibodies have affinity for a particular protein only when in a certain conformation or having a specific modification.

In some embodiments, one or more modifications are made to the fragment crystallizable region (Fc region) of the affinity reagent antibody. The Fc region is the tail region of an antibody that interacts with cell surface receptors and some proteins of the complement system. In other embodiments, the modification is made to a common region far from the target binding region. In this manner, one may obtain a library of antibodies affinity reagents having specificity for desired targets, each antibody chemically modified to include a linked DNA barcode of known sequence. In certain embodiments, the DNA barcode sequence is flanked by common sequences.

In other embodiments, the affinity reagents are aptamers. Aptamers are peptides and nucleic acid molecules that bind specifically to various biological molecules and are useful for in vitro or in vivo localization and quantification of various biological molecules. Aptamers are useful in biotechnological and therapeutic applications as they offer molecular recognition properties that rival that of the commonly used biomolecule, antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. Generally, nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms.

Peptide aptamers are peptides selected or engineered to bind specific target molecules. These proteins consist of one or more peptide loops of variable sequence displayed by a protein scaffold. They can be isolated from combinatorial libraries and, in some cases, modified by directed mutation or rounds of variable region mutagenesis and selection. In vivo, peptide aptamers can bind cellular protein targets and exert biological effects, including interference with the normal protein interactions of their targeted molecules with other proteins. Libraries of peptide aptamers have been used as "mutagens," in studies in which an investigator introduces a library that expresses different peptide aptamers into a cell population, selects for a desired phenotype, and identifies those aptamers associated with that phenotype.

As demonstrated in the Example section herein, genes from multiple HPV strains were cloned and expressed in vitro to produce a library of HPV antigens. When DNA barcodes and their flanking sequences were linked to these antigens, the resulting affinity reagents could detect the presence of particular HPV strain DNA in patient samples.

Like antibody affinity reagents, aptamer affinity reagents comprise a linked DNA barcode sequence. In some cases, the linker is a cleavable protein photocrosslinker, which can be photo-cleaved from the antibody or aptamer. In other cases, the linker is a ligand comprising a DNA barcode which can append to a target with a fusion tag. For example, the linker may be a Halo ligand comprising a barcode sequence appended to a Halo fusion tag. In other cases, the linker comprises a fluorescent probe in addition to the DNA barcode.

Once the library of antibodies is assembled. Each antibody is chemically modified in step 140 to add a linker that includes a unique DNA barcode, which is an identifying sequence flanked at its 5' and 3' ends by a set of common sequences. In certain embodiments, the DNA barcode comprises a nucleotide sequence of GCTGTACGGATT (SEQ ID NO:1). Other DNA barcode sequences are set forth in Table 1. Exemplary linker sequences are set forth in Table 2. The common sequences act as a pair of amplifying sequences. In some embodiments, each barcode sequence (bold font) is flanked by a 5' flanking sequence and a 3' flanking sequence. In some cases, the 5' flanking sequence is (CCACCGCTGAGCAATAACTA; SEQ ID NO:2). In some cases, the 3' flanking sequence is (CGTAGATGAGTCAACGGCCT; SEQ ID NO:3).

TABLE 1

Exemplary Barcode Sequences

| Barcode name | barcode sequence | Barcode SEQ ID NO: |
|---|---|---|
| Halo_BC1 | GTAGTGACAGGT | 4 |
| Halo_BC2 | TCTGTGAAGTCC | 5 |
| Halo_BC3 | ATCAGATCGCCT | 6 |
| Halo_BC4 | AATGTGGTCTCG | 7 |
| Halo_BC5 | CCTCTCCAAACA | 8 |
| Halo_BC6 | TACTGGACAAGG | 9 |
| Halo_BC7 | TATCGGAGTCCT | 10 |
| Halo_BC8 | GGTGGAGTTACT | 11 |
| Halo_BC9 | CGGCTACTATTG | 12 |
| Halo_BC10 | CCGAGCTATGTA | 13 |
| Halo_BC11 | ACTACGTCCAAC | 14 |
| Halo_BC12 | TTCATCCGAACG | 15 |
| Halo_BC13 | CGAAACGCTTAG | 16 |
| Halo_BC14 | GCCTAAGTTCCA | 17 |
| Halo_BC15 | CAATTCCCACGT | 18 |
| Halo_BC16 | CGGTGAGACATA | 19 |
| Halo_BC17 | CTCTGAGGTTTG | 20 |
| Halo_BC18 | TACTGTCACCCA | 21 |
| Halo_BC19 | CAGGAGGTACAT | 22 |
| Halo_BC20 | CTTCCTACAGCA | 23 |
| Halo_BC21 | TAGAAACCGAGG | 24 |

TABLE 1-continued

Exemplary Barcode Sequences

| Barcode name | barcode sequence | Barcode SEQ ID NO: |
|---|---|---|
| Halo_BC22 | GAAAAGCGTACC | 25 |
| Halo_BC23 | CGCTCATAACTC | 26 |
| Halo_BC24 | GGCATATACGAC | 27 |
| Halo_BC25 | GTGCTCTATCAC | 28 |
| Halo_BC26 | GGAGCATTTCAC | 29 |
| Halo_BC27 | ATGGGTCTTCTG | 30 |
| Halo_BC28 | AAGTCCGTGAAC | 31 |
| Halo_BC29 | TGACATAGAGGG | 32 |
| Halo_BC30 | CGTCAATCGTGT | 33 |
| Halo_BC31 | GTTCGAAGCAAC | 34 |
| Halo_BC32 | ACCCGAATTCAC | 35 |
| Halo_BC33 | GAGGACTTCACA | 36 |
| Halo_BC34 | GATTCCACCGTA | 37 |
| Halo_BC35 | GTATTCGCCATG | 38 |
| Halo_BC36 | GCTTGTTATCCG | 39 |
| Halo_BC37 | CGTCCAACTATG | 40 |
| Halo_BC38 | GGTAACAGTGAC | 41 |
| Halo_BC39 | GCGCAAAAGAAG | 42 |
| Halo_BC40 | TGTGGTTGATCG | 43 |
| Halo_BC41 | TGTGGGATTGTG | 44 |
| Halo_BC42 | TGCTTCGGGATA | 45 |
| Halo_BC43 | GACAGCTCGTTA | 46 |
| Halo_BC44 | TAAGAAGCGCTC | 47 |
| Halo_BC45 | CATACACACTCC | 48 |
| Halo_BC46 | TGCCGCCAAAAT | 49 |
| Halo_BC47 | CGGACCTTCTAA | 50 |
| Halo_BC48 | TCTCACGTCAAC | 51 |
| Halo_BC49 | CGCAAGAGAACA | 52 |
| Halo_BC50 | TTAGCTTCCCTG | 53 |
| Halo_BC51 | GAAGCCAAGCAT | 54 |
| Halo_BC52 | TTCGTAGCGTGT | 55 |
| Halo_BC53 | GTCGCTGATCAA | 56 |
| Halo_BC54 | TCAACTGATCGG | 57 |
| Halo_BC55 | CCAGTTTCTACG | 58 |
| Halo_BC56 | ACCCATTGCGAT | 59 |
| Halo_BC57 | TCACCACCCTAT | 60 |
| Halo_BC58 | GGTCTTCACTTC | 61 |
| Halo_BC59 | GTTAGAGATGGG | 62 |

TABLE 1 -continued

Exemplary Barcode Sequences

| Barcode name | barcode sequence | Barcode SEQ ID NO: |
|---|---|---|
| Halo_BC60 | TCTTGCACACTC | 63 |
| Halo_BC61 | TTTTCTCTGCGG | 64 |
| Halo_BC62 | TCAGCCGAGTTA | 65 |
| Halo_BC63 | CTCGTGATCAGA | 66 |
| Halo_BC64 | CCTTTCTCGGAA | 67 |
| Halo_BC65 | ACGCTAGAGCTT | 68 |
| Halo_BC66 | TTCCCCGTTTAG | 69 |
| Halo_BC67 | AGAATCGCAACC | 70 |
| Halo_BC68 | GGAAGGAACTGT | 71 |
| Halo_BC69 | CTTGGCATCTTC | 72 |
| Halo_BC70 | AGGCCGATTTGT | 73 |
| Halo_BC71 | AACAAAGGGTCC | 74 |
| Halo_BC72 | CAATTGGTAGCC | 75 |
| Halo_BC73 | ACCATCGACTCA | 76 |
| Halo_BC74 | CGTGAGATGAAC | 77 |
| Halo_BC75 | CCATGGTCTTGT | 78 |
| Halo_BC76 | CAGATATGAGCGC | 79 |
| Halo_BC77 | GTGTGACAGAGT | 80 |
| Halo_BC78 | ATTGTGTGACGG | 81 |
| Halo_BC79 | CGGTAGTTTGCT | 82 |
| Halo_BC80 | GGACATGTCCAT | 83 |
| Halo_BC81 | TTGAGGGAGACA | 84 |
| Halo_BC82 | CGACATCCTCTA | 85 |
| Halo_BC83 | TGAGCGAGTTCA | 86 |
| Halo_BC84 | GACCTTCGGATT | 87 |
| Halo_BC85 | TGTAGATCCGCA | 88 |
| Halo_BC86 | TGGCACTCTAGA | 89 |
| Halo_BC87 | AACAGTAGTCGG | 90 |
| Halo_BC88 | TCATGCGGAAAG | 91 |
| Halo_BC89 | TCGAATCGTGTC | 92 |
| Halo_BC90 | GGTGTATAGCCA | 93 |
| Halo_BC91 | TTGCAGTGCAAG | 94 |
| Halo_BC92 | CGATTGCAGAAG | 95 |
| Halo_BC93 | CCAGACGTTGTT | 96 |
| Halo_BC94 | TGGTGGCCATAA | 97 |
| Halo_BC95 | CAGAGTCAATGG | 98 |
| Halo_BC96 | CCTATCATTCCC | 99 |

TABLE 1 -continued

Exemplary Barcode Sequences

| Barcode name | barcode sequence | Barcode SEQ ID NO: |
|---|---|---|
| Halo_BC97 | GAGGTATGACTC | 100 |
| Halo_BC98 | CTAGGTCAAGTC | 101 |
| Halo_BC99 | ACTCGGCTTTCA | 102 |
| Halo_BC100 | TTCACAAGCGGA | 103 |

TABLE 2

Exemplary Linker Sequences

| Name of barcode included in linker | Linker: flanking seq-barcode sequence-flanking seq | SEQ ID NO: |
|---|---|---|
| Halo_BC1 | CCACCGCTGAGCAATAACTA GTAGTGACAGGT CGTAGATGAGTCAACGGCCT | 104 |
| Halo_BC2 | CCACCGCTGAGCAATAACTA TCTGTGAAGTCC CGTAGATGAGTCAACGGCCT | 105 |
| Halo_BC3 | CCACCGCTGAGCAATAACTA ATCAGATCGCCT CGTAGATGAGTCAACGGCCT | 106 |
| Halo_BC4 | CCACCGCTGAGCAATAACTA AATGTGGTCTCG CGTAGATGAGTCAACGGCCT | 107 |
| Halo_BC5 | CCACCGCTGAGCAATAACTA CCTCTCCAAACA CGTAGATGAGTCAACGGCCT | 108 |
| Halo_BC6 | CCACCGCTGAGCAATAACTA TACTGGACAAGG CGTAGATGAGTCAACGGCCT | 109 |
| Halo_BC7 | CCACCGCTGAGCAATAACTA TATCGGAGTCCT CGTAGATGAGTCAACGGCCT | 110 |
| Halo_BC8 | CCACCGCTGAGCAATAACTA GGTGGAGTTACT CGTAGATGAGTCAACGGCCT | 111 |
| Halo_BC9 | CCACCGCTGAGCAATAACTA CGGCTACTATTG CGTAGATGAGTCAACGGCCT | 112 |
| Halo_BC10 | CCACCGCTGAGCAATAACTA CCGAGCTATGTA CGTAGATGAGTCAACGGCCT | 113 |
| Halo_BC11 | CCACCGCTGAGCAATAACTA ACTACGTCCAAC CGTAGATGAGTCAACGGCCT | 114 |
| Halo_BC12 | CCACCGCTGAGCAATAACTA TTCATCCGAACG CGTAGATGAGTCAACGGCCT | 115 |
| Halo_BC13 | CCACCGCTGAGCAATAACTA CGAAACGCTTAG CGTAGATGAGTCAACGGCCT | 116 |
| Halo_BC14 | CCACCGCTGAGCAATAACTA GCCTAAGTTCCA CGTAGATGAGTCAACGGCCT | 117 |
| Halo_BC15 | CCACCGCTGAGCAATAACTA CAATTCCCACGT CGTAGATGAGTCAACGGCCT | 118 |
| Halo_BC16 | CCACCGCTGAGCAATAACTA CGGTGAGACATA CGTAGATGAGTCAACGGCCT | 119 |
| Halo_BC17 | CCACCGCTGAGCAATAACTA CTCTGAGGTTTG CGTAGATGAGTCAACGGCCT | 120 |
| Halo_BC18 | CCACCGCTGAGCAATAACTA TACTGTCACCCA CGTAGATGAGTCAACGGCCT | 121 |

TABLE 2 -continued

Exemplary Linker Sequences

| Name of barcode included in linker | Linker: flanking seq-barcode sequence-flanking seq | SEQ ID NO: |
|---|---|---|
| Halo_BC19 | CCACCGCTGAGCAATAACTA CAGGAGGTACAT CGTAGATGAGTCAACGGCCT | 122 |
| Halo_BC20 | CCACCGCTGAGCAATAACTA CTTCCTACAGCA CGTAGATGAGTCAACGGCCT | 123 |
| Halo_BC21 | CCACCGCTGAGCAATAACTA TAGAAACCGAGG CGTAGATGAGTCAACGGCCT | 124 |
| Halo_BC22 | CCACCGCTGAGCAATAACTA GAAAAGCGTACC CGTAGATGAGTCAACGGCCT | 125 |
| Halo_BC23 | CCACCGCTGAGCAATAACTA CGCTCATAACTC CGTAGATGAGTCAACGGCCT | 126 |
| Halo_BC24 | CCACCGCTGAGCAATAACTA GGCATATACGAC CGTAGATGAGTCAACGGCCT | 127 |
| Halo_BC25 | CCACCGCTGAGCAATAACTA GTGCTCTATCAC CGTAGATGAGTCAACGGCCT | 128 |
| Halo_BC26 | CCACCGCTGAGCAATAACTA GGAGCATTTCAC CGTAGATGAGTCAACGGCCT | 129 |
| Halo_BC27 | CCACCGCTGAGCAATAACTA ATGGGTCTTCTG CGTAGATGAGTCAACGGCCT | 130 |
| Halo_BC28 | CCACCGCTGAGCAATAACTA AAGTCCGTGAAC CGTAGATGAGTCAACGGCCT | 131 |
| Halo_BC29 | CCACCGCTGAGCAATAACTA TGACATAGAGGG CGTAGATGAGTCAACGGCCT | 132 |
| Halo_BC30 | CCACCGCTGAGCAATAACTA CGTCAATCGTGT CGTAGATGAGTCAACGGCCT | 133 |
| Halo_BC31 | CCACCGCTGAGCAATAACTA GTTCGAAGCAAC CGTAGATGAGTCAACGGCCT | 134 |
| Halo_BC32 | CCACCGCTGAGCAATAACTA ACCCGAATTCAC CGTAGATGAGTCAACGGCCT | 135 |
| Halo_BC33 | CCACCGCTGAGCAATAACTA GAGGACTTCACA CGTAGATGAGTCAACGGCCT | 136 |
| Halo_BC34 | CCACCGCTGAGCAATAACTA GATTCCACCGTA CGTAGATGAGTCAACGGCCT | 137 |
| Halo_BC35 | CCACCGCTGAGCAATAACTA GTATTCGCCATG CGTAGATGAGTCAACGGCCT | 138 |
| Halo_BC36 | CCACCGCTGAGCAATAACTA GCTTGTTATCCG CGTAGATGAGTCAACGGCCT | 139 |
| Halo_BC37 | CCACCGCTGAGCAATAACTA CGTCCAACTATG CGTAGATGAGTCAACGGCCT | 140 |
| Halo_BC38 | CCACCGCTGAGCAATAACTA GGTAACAGTGAC CGTAGATGAGTCAACGGCCT | 141 |
| Halo_BC39 | CCACCGCTGAGCAATAACTA GCGCAAAAGAAG CGTAGATGAGTCAACGGCCT | 142 |
| Halo_BC40 | CCACCGCTGAGCAATAACTA TGTGGTTGATCG CGTAGATGAGTCAACGGCCT | 143 |
| Halo_BC41 | CCACCGCTGAGCAATAACTA TGTGGGATTGTG CGTAGATGAGTCAACGGCCT | 144 |
| Halo_BC42 | CCACCGCTGAGCAATAACTA TGCTTCGGGATA CGTAGATGAGTCAACGGCCT | 145 |
| Halo_BC43 | CCACCGCTGAGCAATAACTA GACAGCTCGTTA CGTAGATGAGTCAACGGCCT | 146 |
| Halo_BC44 | CCACCGCTGAGCAATAACTA TAAGAAGCGCTC CGTAGATGAGTCAACGGCCT | 147 |
| Halo_BC45 | CCACCGCTGAGCAATAACTA CATACACACTCC CGTAGATGAGTCAACGGCCT | 148 |
| Halo_BC46 | CCACCGCTGAGCAATAACTA TGCCGCCAAAAT CGTAGATGAGTCAACGGCCT | 149 |
| Halo_BC47 | CCACCGCTGAGCAATAACTA CGGACCTTCTAA CGTAGATGAGTCAACGGCCT | 150 |
| Halo_BC48 | CCACCGCTGAGCAATAACTA TCTCACGTCAAC CGTAGATGAGTCAACGGCCT | 151 |
| Halo_BC49 | CCACCGCTGAGCAATAACTA CGCAAGAGAACA CGTAGATGAGTCAACGGCCT | 152 |
| Halo_BC50 | CCACCGCTGAGCAATAACTA TTAGCTTCCCTG CGTAGATGAGTCAACGGCCT | 153 |
| Halo_BC51 | CCACCGCTGAGCAATAACTA GAAGCCAAGCAT CGTAGATGAGTCAACGGCCT | 154 |
| Halo_BC52 | CCACCGCTGAGCAATAACTA TTCGTAGCGTGT CGTAGATGAGTCAACGGCCT | 155 |
| Halo_BC53 | CCACCGCTGAGCAATAACTA GTCGCTGATCAA CGTAGATGAGTCAACGGCCT | 156 |
| Halo_BC54 | CCACCGCTGAGCAATAACTA TCAACTGATCGG CGTAGATGAGTCAACGGCCT | 157 |
| Halo_BC55 | CCACCGCTGAGCAATAACTA CCAGTTTCTACG CGTAGATGAGTCAACGGCCT | 158 |
| Halo_BC56 | CCACCGCTGAGCAATAACTA ACCCATTGCGAT CGTAGATGAGTCAACGGCCT | 159 |
| Halo_BC57 | CCACCGCTGAGCAATAACTA TCACCACCCTAT CGTAGATGAGTCAACGGCCT | 160 |
| Halo_BC58 | CCACCGCTGAGCAATAACTA GGTCTTCACTTC CGTAGATGAGTCAACGGCCT | 161 |
| Halo_BC59 | CCACCGCTGAGCAATAACTA GTTAGAGATGGG CGTAGATGAGTCAACGGCCT | 162 |
| Halo_BC60 | CCACCGCTGAGCAATAACTA TCTTGCACACTC CGTAGATGAGTCAACGGCCT | 163 |
| Halo_BC61 | CCACCGCTGAGCAATAACTA TTTTCTCTGCGG CGTAGATGAGTCAACGGCCT | 164 |
| Halo_BC62 | CCACCGCTGAGCAATAACTA TCAGCCGAGTTA CGTAGATGAGTCAACGGCCT | 165 |
| Halo_BC63 | CCACCGCTGAGCAATAACTA CTCGTGATCAGA CGTAGATGAGTCAACGGCCT | 166 |
| Halo_BC64 | CCACCGCTGAGCAATAACTA CCTTTCTCGGAA CGTAGATGAGTCAACGGCCT | 167 |
| Halo_BC65 | CCACCGCTGAGCAATAACTA ACGCTAGAGCTT CGTAGATGAGTCAACGGCCT | 168 |
| Halo_BC66 | CCACCGCTGAGCAATAACTA TTCCCCGTTTAG CGTAGATGAGTCAACGGCCT | 169 |

TABLE 2 -continued
Exemplary Linker Sequences

| Name of barcode included in linker | Linker: flanking seq-barcode sequence-flanking seq | SEQ ID NO: |
|---|---|---|
| Halo_BC67 | CCACCGCTGAGCAATAACTA AGAATCGCAACC CGTAGATGAGTCAACGGCCT | 170 |
| Halo_BC68 | CCACCGCTGAGCAATAACTA GGAAGGAACTGT CGTAGATGAGTCAACGGCCT | 171 |
| Halo_BC69 | CCACCGCTGAGCAATAACTA CTTGGCATCTTC CGTAGATGAGTCAACGGCCT | 172 |
| Halo_BC70 | CCACCGCTGAGCAATAACTA AGGCCGATTTGT CGTAGATGAGTCAACGGCCT | 173 |
| Halo_BC71 | CCACCGCTGAGCAATAACTA AACAAAGGGTCC CGTAGATGAGTCAACGGCCT | 174 |
| Halo_BC72 | CCACCGCTGAGCAATAACTA CAATTGGTAGCC CGTAGATGAGTCAACGGCCT | 175 |
| Halo_BC73 | CCACCGCTGAGCAATAACTA ACCATCGACTCA CGTAGATGAGTCAACGGCCT | 176 |
| Halo_BC74 | CCACCGCTGAGCAATAACTA CGTGAGATGAAC CGTAGATGAGTCAACGGCCT | 177 |
| Halo_BC75 | CCACCGCTGAGCAATAACTA CCATGGTCTTGT CGTAGATGAGTCAACGGCCT | 178 |
| Halo_BC76 | CCACCGCTGAGCAATAACTA AGATATGAGCGC CGTAGATGAGTCAACGGCCT | 179 |
| Halo_BC77 | CCACCGCTGAGCAATAACTA GTGTGACAGAGT CGTAGATGAGTCAACGGCCT | 180 |
| Halo_BC78 | CCACCGCTGAGCAATAACTA ATTGTGTGACGG CGTAGATGAGTCAACGGCCT | 181 |
| Halo_BC79 | CCACCGCTGAGCAATAACTA CGGTAGTTTGCT CGTAGATGAGTCAACGGCCT | 182 |
| Halo_BC80 | CCACCGCTGAGCAATAACTA GGACATGTCCAT CGTAGATGAGTCAACGGCCT | 183 |
| Halo_BC81 | CCACCGCTGAGCAATAACTA TTGAGGGAGACA CGTAGATGAGTCAACGGCCT | 184 |
| Halo_BC82 | CCACCGCTGAGCAATAACTA CGACATCCTCTA CGTAGATGAGTCAACGGCCT | 185 |
| Halo_BC83 | CCACCGCTGAGCAATAACTA TGAGCGAGTTCA CGTAGATGAGTCAACGGCCT | 186 |
| Halo_BC84 | CCACCGCTGAGCAATAACTA GACCTTCGGATT CGTAGATGAGTCAACGGCCT | 187 |
| Halo_BC85 | CCACCGCTGAGCAATAACTA TGTAGATCCGCA CGTAGATGAGTCAACGGCCT | 188 |
| Halo_BC86 | CCACCGCTGAGCAATAACTA TGGCACTCTAGA CGTAGATGAGTCAACGGCCT | 189 |
| Halo_BC87 | CCACCGCTGAGCAATAACTA AACAGTAGTCGG CGTAGATGAGTCAACGGCCT | 190 |
| Halo_BC88 | CCACCGCTGAGCAATAACTA TCATGCGGAAAG CGTAGATGAGTCAACGGCCT | 191 |
| Halo_BC89 | CCACCGCTGAGCAATAACTA TCGAATCGTGTC CGTAGATGAGTCAACGGCCT | 192 |
| Halo_BC90 | CCACCGCTGAGCAATAACTA GGTGTATAGCCA CGTAGATGAGTCAACGGCCT | 193 |
| Halo_BC91 | CCACCGCTGAGCAATAACTA TTGCAGTGCAAG CGTAGATGAGTCAACGGCCT | 194 |
| Halo_BC92 | CCACCGCTGAGCAATAACTA CGATTGCAGAAG CGTAGATGAGTCAACGGCCT | 195 |
| Halo_BC93 | CCACCGCTGAGCAATAACTA CCAGACGTTGTT CGTAGATGAGTCAACGGCCT | 196 |
| Halo_BC94 | CCACCGCTGAGCAATAACTA TGGTGGCCATAA CGTAGATGAGTCAACGGCCT | 197 |
| Halo_BC95 | CCACCGCTGAGCAATAACTA CAGAGTCAATGG CGTAGATGAGTCAACGGCCT | 198 |
| Halo_BC96 | CCACCGCTGAGCAATAACTA CCTATCATTCCC CGTAGATGAGTCAACGGCCT | 199 |
| Halo_BC97 | CCACCGCTGAGCAATAACTA GAGGTATGACTC CGTAGATGAGTCAACGGCCT | 200 |
| Halo_BC98 | CCACCGCTGAGCAATAACTA CTAGGTCAAGTC CGTAGATGAGTCAACGGCCT | 201 |
| Halo_BC99 | CCACCGCTGAGCAATAACTA ACTCGGCTTTCA CGTAGATGAGTCAACGGCCT | 202 |
| Halo_BC100 | CCACCGCTGAGCAATAACTA TTCACAAGCGGA CGTAGATGAGTCAACGGCCT | 203 |

Methods

In another aspect, provided herein are methods for multiplexed detection and measurement of multiple targets in a sample using affinity reagents that comprise a unique DNA barcode. In some cases, the method comprises contacting affinity reagents comprising unique DNA barcodes to a sample under conditions that promote binding of the affinity reagents to target antigens when present in said sample. The methods provided herein can employ a variety of affinity reagents, including those favored by a user, in a multiplexed set to measure the abundance of their respective targets in a sample. The methods provided herein permit measurement of the levels of proteins or any detectable antigens in high throughput. This method uses available antibodies which enables the user to use those antibodies that have the best specification for purpose. This does not require the user to remain within a closed system such as a proprietary set of aptamers or a set of reagents for which binding data are not public. The method will have a wide dynamic range and can be multiplexed in the thousands.

In cases in which the affinity reagents are antibodies and the targets are antigens, antibodies that are bound to their target antigens can be separated from unbound antibodies. Any method of uniquely detecting and measuring the DNA barcodes can be used. In some embodiments, the DNA barcode associated with the affinity reagent is amplified, such as by polymerase chain reaction (PCR) or another amplification technique, and the amplified barcode DNA is subjected to DNA sequencing to provide a measure of target protein in the contacted sample. In other cases, the DNA barcode is detected using, for example, a nucleic acid array or aptamers.

Referring to the flow chart of FIG. 1, the methods in some cases comprise obtaining a biological sample (see step 110).

In step 120, the user may define a list of target proteins (or other targets) to be detected and quantified in the sample. In step 130, affinity reagents that specifically recognize each of the targets on the list are prepared by linking a unique barcode to antibodies or aptamers having affinity for those targets.

In some embodiments, protein measurement comprises separating bound antibodies from unbound antibodies. In some cases, the sample is brought into contact with the antibody mix under conditions that promote binding of affinity reagents to their targets if presented in the sample. Unbound antibodies are washed away in step 160.

Any appropriate method can be used to detect and measure binding of affinity reagents to their targets in the sample. For example, referring to step 170 of FIG. 1, PCR-based amplification can be performed directly on the sample using primers that correspond to the sequences that flank the bar code. As described above, the flanking amplifying sequences can comprise nucleotide sequences of CCACCGCTGAGCAATAACTA (SEQ ID NO:2) and CGTAGATGAGTCAACGGCCT (SEQ ID NO:3). By sequencing the resulting amplified DNA, the number of each type of target can be assessed based on the barcode. In other embodiments, linkers containing the barcodes are released from the samples by photo cleavage or a chemical cleavage, and then collected and used to run a PCR reaction as above. The resulting amplified DNA is subjected to DNA sequencing to assess the number of each type of target based on the barcode. In yet other embodiments, the linkers containing both the barcodes and fluorescent tag are released from the samples by photo cleavage, and then collected. They are then used to hybridize to a DNA microarray that specifically recognizes the barcodes.

The terms "quantity", "amount" and "level" are synonymous and generally well-understood in the art. The terms as used herein may particularly refer to an absolute quantification of a target molecule in a sample, or to a relative quantification of a target molecule in a sample, i.e., relative to another value such as relative to a reference value or to a range of values indicating a base-line expression of the biomarker. These values or ranges can be obtained from a single subject (e.g., human patient) or aggregated from a group of subjects. In some cases, target measurements are compared to a standard or set of standards.

In a further aspect, provided herein are methods for detecting and quantifying a subject's immune response to a disease (e.g., cancer, autoimmune disorder) or infectious agent such as a pathogenic microorganism. In such cases, affinity reagents are selected for their affinity for molecular targets associated with a particular disease or infectious agent. Advantageously, the affinity reagents described herein are well suited for multiplexed screening of a sample for many different infections. For example, one may assay a sample for many infections simultaneously to see which induced an immune response and to which infection-associated proteins triggered the response. Samples appropriate for use according to the methods provided herein include biological samples such as, for example, blood, plasma, serum, urine, saliva, tissues, cells, organs, organisms or portions thereof (e.g., mosquitoes, bacteria, plants or plant material), patient samples (e.g., feces or body fluids, such as urine, blood, serum, plasma, or cerebrospinal fluid), food samples, drinking water, and agricultural products.

In certain embodiments, affinity reagents described herein are used to detect and, in some cases, monitor a subject's immune response to an infectious pathogen. By way of example, pathogens may comprise viruses including, without limitation, flaviruses, human immunodeficiency virus (HIV), Ebola virus, single stranded RNA viruses, single stranded DNA viruses, double-stranded RNA viruses, double-stranded DNA viruses. Other pathogens include but are not limited to parasites (e.g., malaria parasites and other protozoan and metazoan pathogens (Plasmodia species, *Leishmania* species, *Schistosoma* species, *Trypanosoma* species)), bacteria (e.g., Mycobacteria, in particular, *M. tuberculosis, Salmonella*, Streptococci, *E. coli*, Staphylococci), fungi (e.g., *Candida* species, *Aspergillus* species, *Pneumocystis jirovecii* and other *Pneumocystis* species), and prions. In some cases, the pathogenic microorganism, e.g. pathogenic bacteria, may be one which causes cancer in certain human cell types.

In certain embodiments, the methods detect viruses including, without limitation, the human-pathogenic viruses such Zika virus (e.g., Zika strain from the Americas, ZIKV), yellow fever virus, and dengue virus serotypes 1 (DENV1) and 3 (DENV3), and closely related viruses such as the chikungunya virus (CHIKV).

The terms "detect" or "detection" as used herein indicate the determination of the existence, presence or fact of a target molecule in a limited portion of space, including but not limited to a sample, a reaction mixture, a molecular complex and a substrate including a platform and an array. Detection is "quantitative" when it refers, relates to, or involves the measurement of quantity or amount of the target or signal (also referred as quantitation), which includes but is not limited to any analysis designed to determine the amounts or proportions of the target or signal. Detection is "qualitative" when it refers, relates to, or involves identification of a quality or kind of the target or signal in terms of relative abundance to another target or signal, which is not quantified.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or include non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadeno sine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain, and an organic compound, e.g., a compound that can act as a nucleic acid cleavage agent.

Articles of Manufacture

In another aspect, provided herein are articles of manufacture useful for detecting target molecules, including infection-associated or disease-associated molecules (e.g., cancer associated). In certain embodiments, the article of manufacture is a kit for detecting an immune response to a pathogen, where the kit comprises a plurality of affinity reagents, each of which comprises a linked DNA barcode, and one or more of reagents to amplify DNA barcodes using polymerase chain reaction. Preferably, the linked DNA barcode is flanked by a pair of amplifying nucleotide sequences, and each affinity reagent has a different identifying barcode sequence from other affinity reagents. Optionally, a kit can further include instructions for performing the detection and/or amplification methods described herein.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

The indefinite articles "a" and "an," as used herein in the specification and in the claims, unless clearly indicated to the contrary, should be understood to mean "at least one." Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Unless otherwise indicated, any nucleic acid sequences are written left to right in 5' to 3' orientation; amino acid sequences are written left to right in amino to carboxy orientation, respectively.

Schematic flow charts included are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention is further illustrated by the following Examples, which in no way should be construed as further limiting. The entire contents of all of the references (including literature references, issued patents, published patent applications, and co-pending patent applications) cited throughout this application are hereby expressly incorporated herein by reference.

EXAMPLE

Figure 2:
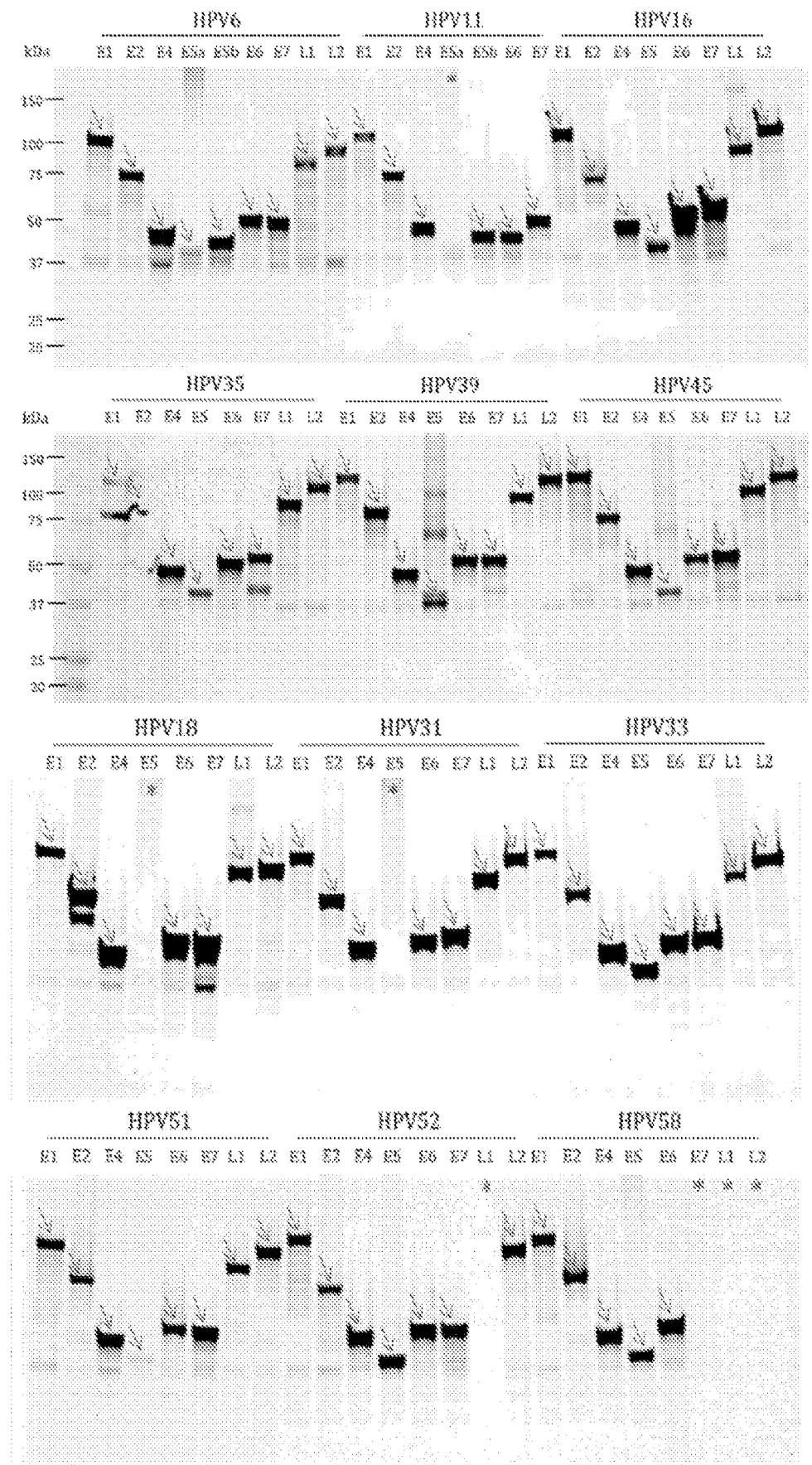
FIG. 2 demonstrates cloning and protein expression of the HPV proteome. An SDS-PAGE gel shows the expression of antigens of different HPV subtypes. (*) indicates an unexpressed protein. Further experiments confirmed expression of HPV58 E7, L1, and L2.

To develop a quantitative, multiplexed, bar-coded antigen library for detection of immune responses in pathogen induced cancers, we cloned 97 HPV genes from the HPV strains 6, 16, 18, 31, 33, 35, 39, 45, 51, 52, and 58 into the pJFT7-3XFLAG-Halo vector. This vector includes two fusion tags 3XFLAG and Halo fusion. As shown in FIG. 2, the HPV proteome was expressed in a cell-free human IVT system with a 97% success rate. Except for the HPV11 E5a and HPV 31 E5 antigens, full-length proteins for the HPV proteome were successfully expressed.

Figure 3:
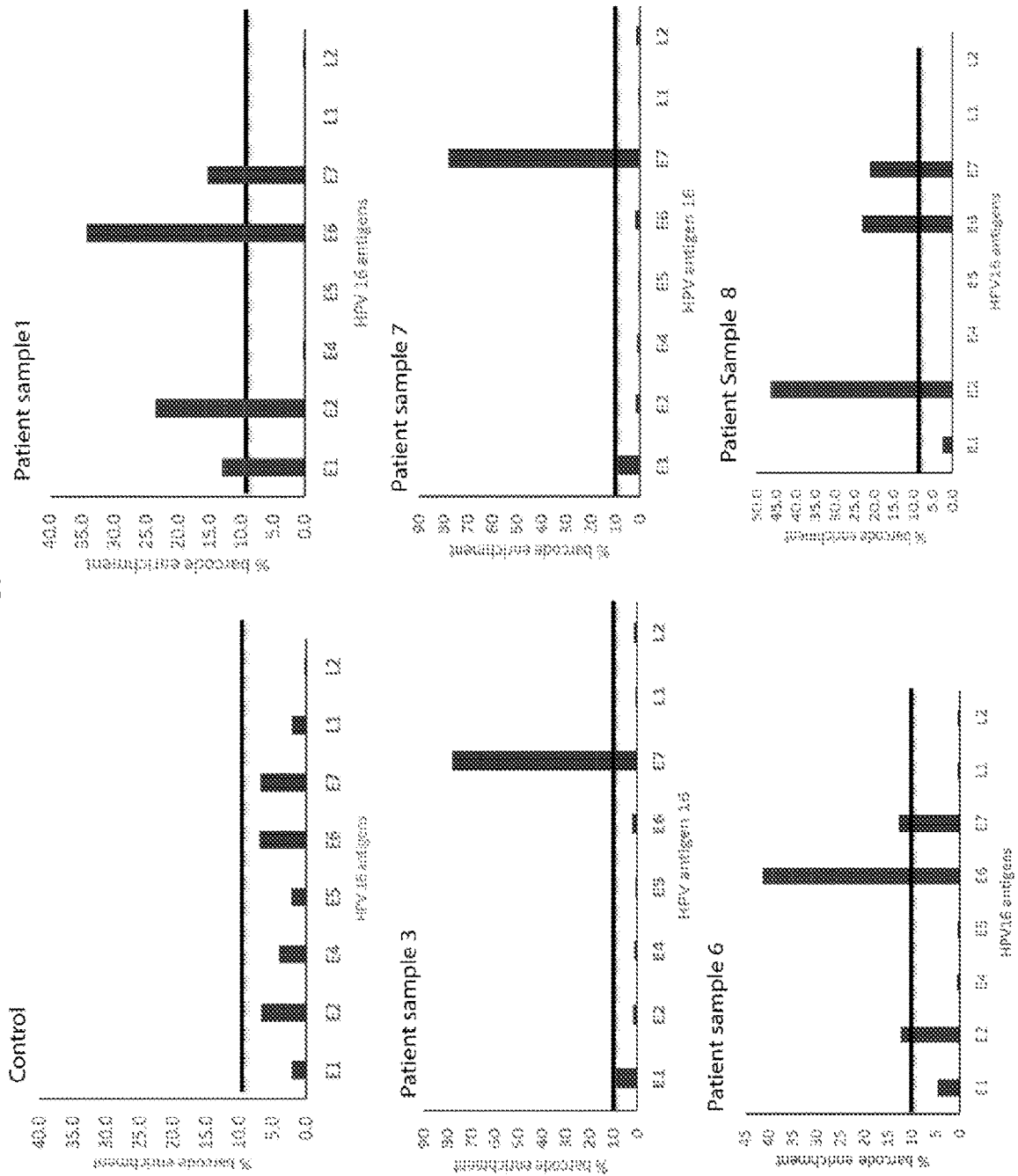
FIG. 3 demonstrates immune response screening of OPC patient sera. Percent barcode enrichment of control and OPC patient sera after barcode amplification and next generation sequencing.
Figure 4:
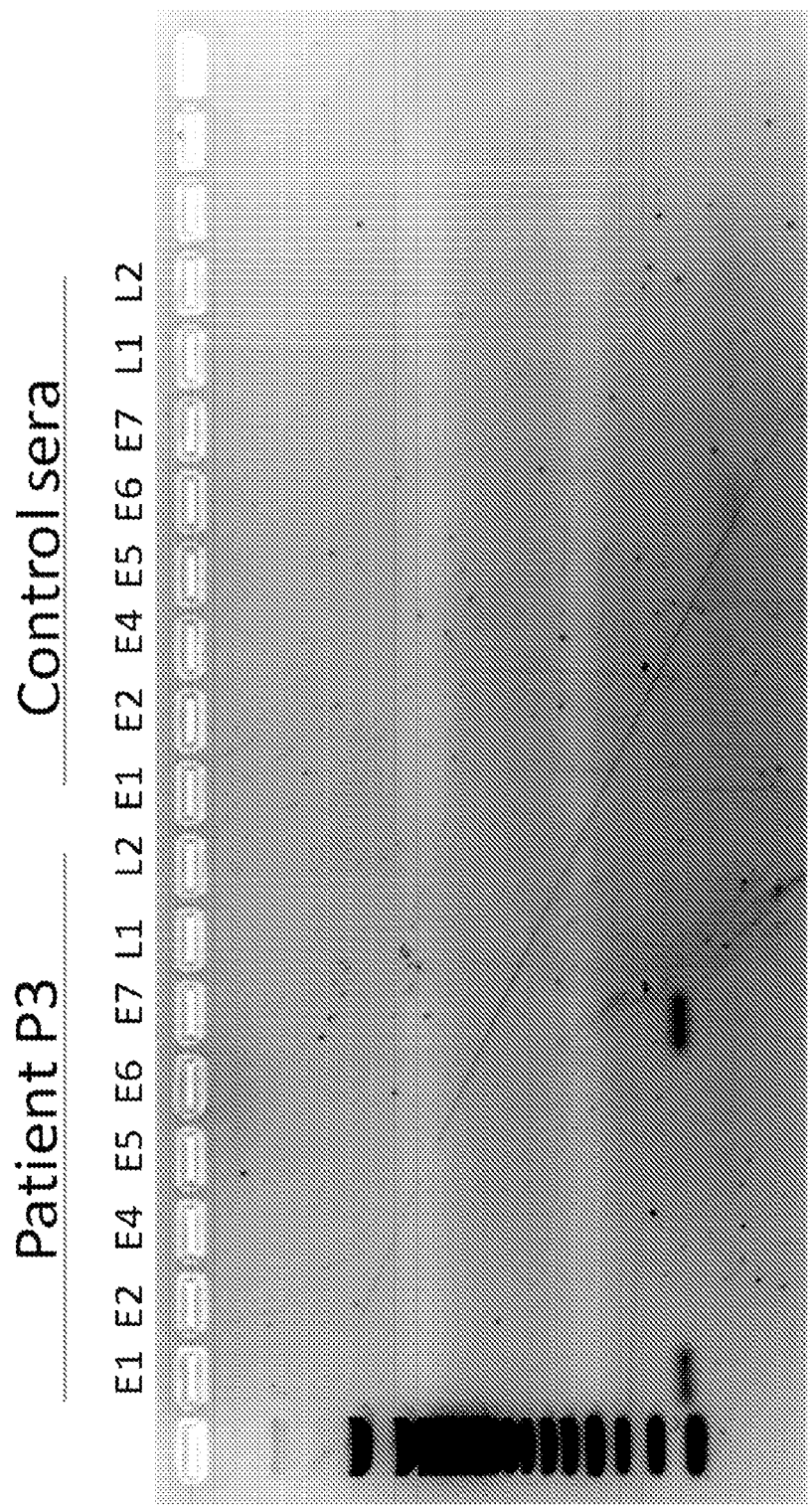
FIG. 4 is an image of a DNA gel showing the enrichment of antibodies against E1 and E7 antigens in OPC patient P3 with barcode specific primers.

Unique DNA barcodes (attached to Halo ligand) were appended to 20 antigens from HPV strains 16, 18 (high risk HPV strains) and 6 (a low risk HPV strain). After capturing the expressed and barcoded HPV antigens with FLAG magnetic beads we combined all the HPV antigens into a single protein cocktail. This barcoded protein cocktail was then probed against 10 HPV infected OPC patient samples and 10 control samples. After capturing in protein, A/G magnetic beads we amplified the barcodes and ran the samples on NextSeq after multiplexing. From our sequencing run we obtained 450K reads per sample with 71% mapping ratio to our barcodes. The normalized percentage of each barcode showed distinct enrichment of certain HPV antigens in the OPC patient samples (FIG. 3). In contrast, most of the control samples showed only less than 10% barcode enrichment for the HPV antigens. This clearly demonstrates that the barcoded HPV proteome can be utilized to quantify the immune responses for certain HPV antigens in OPC patient sera. We observed a heterogeneous immune response for the HPV positive OPC serum sample, where antibodies were detected for E1, E2, E6 and E7 HPV 16 antigens. We also detected similar patterns for antibody profiles when we amplified our unique barcodes with barcode specific PCR primers (FIG. 4).

What is claimed is:

1. A composition comprising a plurality of modified affinity reagents, each affinity reagent of the plurality comprising a unique identifying nucleotide sequence relative to other affinity reagents of the plurality, wherein each identifying nucleotide sequence is flanked by a first amplifying nucleotide sequence and a second amplifying nucleotide sequence, wherein the unique identifying nucleotide sequences of the plurality comprise SEQ ID No:104.

* * * * *

```
                        SEQUENCE LISTING

<160> NUMBER OF SEQ ID NOS: 203

<210> SEQ ID NO 1
<211> LENGTH: 12
<212> TYPE: DNA
<213> ORGANISM: Artificial Sequence
<220> FEATURE:
<223> OTHER INFORMATION: synthetic

<400> SEQUENCE: 1
gctgtacgga tt                                                          12

<210> SEQ ID NO 2
<211> LENGTH: 20
<212> TYPE: DNA
<213> ORGANISM: Artificial Sequence
<220> FEATURE:
<223> OTHER INFORMATION: synthetic

<400> SEQUENCE: 2
ccaccgctga gcaataacta                                                  20

<210> SEQ ID NO 3
<211> LENGTH: 20
<212> TYPE: DNA
<213> ORGANISM: Artificial Sequence
<220> FEATURE:
<223> OTHER INFORMATION: synthetic

<400> SEQUENCE: 3
cgtagatgag tcaacggcct                                                  20

<210> SEQ ID NO 4
<211> LENGTH: 12
<212> TYPE: DNA
<213> ORGANISM: Artificial Sequence
<220> FEATURE:
<223> OTHER INFORMATION: synthetic

<400> SEQUENCE: 4
gtagtgacag gt                                                          12

<210> SEQ ID NO 5
<211> LENGTH: 12
<212> TYPE: DNA
<213> ORGANISM: Artificial Sequence
<220> FEATURE:
<223> OTHER INFORMATION: synthetic

<400> SEQUENCE: 5
tctgtgaagt cc                                                          12

<210> SEQ ID NO 6
<211> LENGTH: 12
<212> TYPE: DNA
<213> ORGANISM: Artificial Sequence
<220> FEATURE:
<223> OTHER INFORMATION: synthetic

<400> SEQUENCE: 6
atcagatcgc ct                                                          12
```

```
<210> SEQ ID NO 7
<211> LENGTH: 12
<212> TYPE: DNA
<213> ORGANISM: Artificial Sequence
<220> FEATURE:
<223> OTHER INFORMATION: synthetic

<400> SEQUENCE: 7
aatgtggtct cg                                                              12

<210> SEQ ID NO 8
<211> LENGTH: 12
<212> TYPE: DNA
<213> ORGANISM: Artificial Sequence
<220> FEATURE:
<223> OTHER INFORMATION: synthetic

<400> SEQUENCE: 8
cctctccaaa ca                                                              12

<210> SEQ ID NO 9
<211> LENGTH: 12
<212> TYPE: DNA
<213> ORGANISM: Artificial Sequence
<220> FEATURE:
<223> OTHER INFORMATION: synthetic

<400> SEQUENCE: 9
tactggacaa gg                                                              12

<210> SEQ ID NO 10
<211> LENGTH: 12
<212> TYPE: DNA
<213> ORGANISM: Artificial Sequence
<220> FEATURE:
<223> OTHER INFORMATION: synthetic

<400> SEQUENCE: 10
tatcggagtc ct                                                              12

<210> SEQ ID NO 11
<211> LENGTH: 12
<212> TYPE: DNA
<213> ORGANISM: Artificial Sequence
<220> FEATURE:
<223> OTHER INFORMATION: synthetic

<400> SEQUENCE: 11
ggtggagtta ct                                                              12

<210> SEQ ID NO 12
<211> LENGTH: 12
<212> TYPE: DNA
<213> ORGANISM: Artificial Sequence
<220> FEATURE:
<223> OTHER INFORMATION: synthetic

<400> SEQUENCE: 12
cggctactat tg                                                              12

<210> SEQ ID NO 13
<211> LENGTH: 12
<212> TYPE: DNA
<213> ORGANISM: Artificial Sequence
<220> FEATURE:
```

<223> OTHER INFORMATION: synthetic

<400> SEQUENCE: 13
ccgagctatg ta                                                          12

<210> SEQ ID NO 14
<211> LENGTH: 12
<212> TYPE: DNA
<213> ORGANISM: Artificial Sequence
<220> FEATURE:
<223> OTHER INFORMATION: synthetic

<400> SEQUENCE: 14
actacgtcca ac                                                          12

<210> SEQ ID NO 15
<211> LENGTH: 12
<212> TYPE: DNA
<213> ORGANISM: Artificial Sequence
<220> FEATURE:
<223> OTHER INFORMATION: synthetic

<400> SEQUENCE: 15
ttcatccgaa cg                                                          12

<210> SEQ ID NO 16
<211> LENGTH: 12
<212> TYPE: DNA
<213> ORGANISM: Artificial Sequence
<220> FEATURE:
<223> OTHER INFORMATION: synthetic

<400> SEQUENCE: 16
cgaaacgctt ag                                                          12

<210> SEQ ID NO 17
<211> LENGTH: 12
<212> TYPE: DNA
<213> ORGANISM: Artificial Sequence
<220> FEATURE:
<223> OTHER INFORMATION: synthetic

<400> SEQUENCE: 17
gcctaagttc ca                                                          12

<210> SEQ ID NO 18
<211> LENGTH: 12
<212> TYPE: DNA
<213> ORGANISM: Artificial Sequence
<220> FEATURE:
<223> OTHER INFORMATION: synthetic

<400> SEQUENCE: 18
caattcccac gt                                                          12

<210> SEQ ID NO 19
<211> LENGTH: 12
<212> TYPE: DNA
<213> ORGANISM: Artificial Sequence
<220> FEATURE:
<223> OTHER INFORMATION: synthetic

<400> SEQUENCE: 19
cggtgagaca ta                                                          12

```
<210> SEQ ID NO 20
<211> LENGTH: 12
<212> TYPE: DNA
<213> ORGANISM: Artificial Sequence
<220> FEATURE:
<223> OTHER INFORMATION: synthetic

<400> SEQUENCE: 20
ctctgaggtt tg                                                           12

<210> SEQ ID NO 21
<211> LENGTH: 12
<212> TYPE: DNA
<213> ORGANISM: Artificial Sequence
<220> FEATURE:
<223> OTHER INFORMATION: synthetic

<400> SEQUENCE: 21
tactgtcacc ca                                                           12

<210> SEQ ID NO 22
<211> LENGTH: 12
<212> TYPE: DNA
<213> ORGANISM: Artificial Sequence
<220> FEATURE:
<223> OTHER INFORMATION: synthetic

<400> SEQUENCE: 22
caggaggtac at                                                           12

<210> SEQ ID NO 23
<211> LENGTH: 12
<212> TYPE: DNA
<213> ORGANISM: Artificial Sequence
<220> FEATURE:
<223> OTHER INFORMATION: synthetic

<400> SEQUENCE: 23
cttcctacag ca                                                           12

<210> SEQ ID NO 24
<211> LENGTH: 12
<212> TYPE: DNA
<213> ORGANISM: Artificial Sequence
<220> FEATURE:
<223> OTHER INFORMATION: synthetic

<400> SEQUENCE: 24
tagaaaccga gg                                                           12

<210> SEQ ID NO 25
<211> LENGTH: 12
<212> TYPE: DNA
<213> ORGANISM: Artificial Sequence
<220> FEATURE:
<223> OTHER INFORMATION: synthetic

<400> SEQUENCE: 25
gaaaagcgta cc                                                           12

<210> SEQ ID NO 26
<211> LENGTH: 12
<212> TYPE: DNA
<213> ORGANISM: Artificial Sequence
<220> FEATURE:
<223> OTHER INFORMATION: synthetic
```

```
<400> SEQUENCE: 26
cgctcataac tc                                                         12

<210> SEQ ID NO 27
<211> LENGTH: 12
<212> TYPE: DNA
<213> ORGANISM: Artificial Sequence
<220> FEATURE:
<223> OTHER INFORMATION: synthetic

<400> SEQUENCE: 27
ggcatatacg ac                                                         12

<210> SEQ ID NO 28
<211> LENGTH: 12
<212> TYPE: DNA
<213> ORGANISM: Artificial Sequence
<220> FEATURE:
<223> OTHER INFORMATION: synthetic

<400> SEQUENCE: 28
gtgctctatc ac                                                         12

<210> SEQ ID NO 29
<211> LENGTH: 12
<212> TYPE: DNA
<213> ORGANISM: Artificial Sequence
<220> FEATURE:
<223> OTHER INFORMATION: synthetic

<400> SEQUENCE: 29
ggagcatttc ac                                                         12

<210> SEQ ID NO 30
<211> LENGTH: 12
<212> TYPE: DNA
<213> ORGANISM: Artificial Sequence
<220> FEATURE:
<223> OTHER INFORMATION: synthetic

<400> SEQUENCE: 30
atgggtcttc tg                                                         12

<210> SEQ ID NO 31
<211> LENGTH: 12
<212> TYPE: DNA
<213> ORGANISM: Artificial Sequence
<220> FEATURE:
<223> OTHER INFORMATION: synthetic

<400> SEQUENCE: 31
aagtccgtga ac                                                         12

<210> SEQ ID NO 32
<211> LENGTH: 12
<212> TYPE: DNA
<213> ORGANISM: Artificial Sequence
<220> FEATURE:
<223> OTHER INFORMATION: synthetic

<400> SEQUENCE: 32
tgacatagag gg                                                         12

<210> SEQ ID NO 33
<211> LENGTH: 12
```

```
<212> TYPE: DNA
<213> ORGANISM: Artificial Sequence
<220> FEATURE:
<223> OTHER INFORMATION: synthetic

<400> SEQUENCE: 33
cgtcaatcgt gt                                                              12

<210> SEQ ID NO 34
<211> LENGTH: 12
<212> TYPE: DNA
<213> ORGANISM: Artificial Sequence
<220> FEATURE:
<223> OTHER INFORMATION: synthetic

<400> SEQUENCE: 34
gttcgaagca ac                                                              12

<210> SEQ ID NO 35
<211> LENGTH: 12
<212> TYPE: DNA
<213> ORGANISM: Artificial Sequence
<220> FEATURE:
<223> OTHER INFORMATION: synthetic

<400> SEQUENCE: 35
acccgaattc ac                                                              12

<210> SEQ ID NO 36
<211> LENGTH: 12
<212> TYPE: DNA
<213> ORGANISM: Artificial Sequence
<220> FEATURE:
<223> OTHER INFORMATION: synthetic

<400> SEQUENCE: 36
gaggacttca ca                                                              12

<210> SEQ ID NO 37
<211> LENGTH: 12
<212> TYPE: DNA
<213> ORGANISM: Artificial Sequence
<220> FEATURE:
<223> OTHER INFORMATION: synthetic

<400> SEQUENCE: 37
gattccaccg ta                                                              12

<210> SEQ ID NO 38
<211> LENGTH: 12
<212> TYPE: DNA
<213> ORGANISM: Artificial Sequence
<220> FEATURE:
<223> OTHER INFORMATION: synthetic

<400> SEQUENCE: 38
gtattcgcca tg                                                              12

<210> SEQ ID NO 39
<211> LENGTH: 12
<212> TYPE: DNA
<213> ORGANISM: Artificial Sequence
<220> FEATURE:
<223> OTHER INFORMATION: synthetic

<400> SEQUENCE: 39
```
gcttgttatc cg                                                              12

<210> SEQ ID NO 40
<211> LENGTH: 12
<212> TYPE: DNA
<213> ORGANISM: Artificial Sequence
<220> FEATURE:
<223> OTHER INFORMATION: synthetic

<400> SEQUENCE: 40
cgtccaacta tg                                                              12

<210> SEQ ID NO 41
<211> LENGTH: 12
<212> TYPE: DNA
<213> ORGANISM: Artificial Sequence
<220> FEATURE:
<223> OTHER INFORMATION: synthetic

<400> SEQUENCE: 41
ggtaacagtg ac                                                              12

<210> SEQ ID NO 42
<211> LENGTH: 12
<212> TYPE: DNA
<213> ORGANISM: Artificial Sequence
<220> FEATURE:
<223> OTHER INFORMATION: synthetic

<400> SEQUENCE: 42
gcgcaaaaga ag                                                              12

<210> SEQ ID NO 43
<211> LENGTH: 12
<212> TYPE: DNA
<213> ORGANISM: Artificial Sequence
<220> FEATURE:
<223> OTHER INFORMATION: syntehtic

<400> SEQUENCE: 43
tgtggttgat cg                                                              12

<210> SEQ ID NO 44
<211> LENGTH: 12
<212> TYPE: DNA
<213> ORGANISM: Artificial Sequence
<220> FEATURE:
<223> OTHER INFORMATION: synthetic

<400> SEQUENCE: 44
tgtgggattg tg                                                              12

<210> SEQ ID NO 45
<211> LENGTH: 12
<212> TYPE: DNA
<213> ORGANISM: Artificial Sequence
<220> FEATURE:
<223> OTHER INFORMATION: synthetic

<400> SEQUENCE: 45
tgcttcggga ta                                                              12

<210> SEQ ID NO 46
<211> LENGTH: 12
<212> TYPE: DNA
<213> ORGANISM: Artificial Sequence

```
<220> FEATURE:
<223> OTHER INFORMATION: synthetic

<400> SEQUENCE: 46
gacagctcgt ta                                                              12

<210> SEQ ID NO 47
<211> LENGTH: 12
<212> TYPE: DNA
<213> ORGANISM: Artificial Sequence
<220> FEATURE:
<223> OTHER INFORMATION: synthetic

<400> SEQUENCE: 47
taagaagcgc tc                                                              12

<210> SEQ ID NO 48
<211> LENGTH: 12
<212> TYPE: DNA
<213> ORGANISM: Artificial Sequence
<220> FEATURE:
<223> OTHER INFORMATION: synthetic

<400> SEQUENCE: 48
catacacact cc                                                              12

<210> SEQ ID NO 49
<211> LENGTH: 12
<212> TYPE: DNA
<213> ORGANISM: Artificial Sequence
<220> FEATURE:
<223> OTHER INFORMATION: syntehtic

<400> SEQUENCE: 49
tgccgccaaa at                                                              12

<210> SEQ ID NO 50
<211> LENGTH: 12
<212> TYPE: DNA
<213> ORGANISM: Artificial Sequence
<220> FEATURE:
<223> OTHER INFORMATION: synthetic

<400> SEQUENCE: 50
cggaccttct aa                                                              12

<210> SEQ ID NO 51
<211> LENGTH: 12
<212> TYPE: DNA
<213> ORGANISM: Artificial Sequence
<220> FEATURE:
<223> OTHER INFORMATION: synthetic

<400> SEQUENCE: 51
tctcacgtca ac                                                              12

<210> SEQ ID NO 52
<211> LENGTH: 12
<212> TYPE: DNA
<213> ORGANISM: Artificial Sequence
<220> FEATURE:
<223> OTHER INFORMATION: synthetic

<400> SEQUENCE: 52
cgcaagagaa ca                                                              12
```

<210> SEQ ID NO 53
<211> LENGTH: 12
<212> TYPE: DNA
<213> ORGANISM: Artificial Sequence
<220> FEATURE:
<223> OTHER INFORMATION: synthetic

<400> SEQUENCE: 53
ttagcttccc tg                                                          12

<210> SEQ ID NO 54
<211> LENGTH: 12
<212> TYPE: DNA
<213> ORGANISM: Artificial Sequence
<220> FEATURE:
<223> OTHER INFORMATION: synthetic

<400> SEQUENCE: 54
gaagccaagc at                                                          12

<210> SEQ ID NO 55
<211> LENGTH: 12
<212> TYPE: DNA
<213> ORGANISM: Artificial Sequence
<220> FEATURE:
<223> OTHER INFORMATION: synthetic

<400> SEQUENCE: 55
ttcgtagcgt gt                                                          12

<210> SEQ ID NO 56
<211> LENGTH: 12
<212> TYPE: DNA
<213> ORGANISM: Artificial Sequence
<220> FEATURE:
<223> OTHER INFORMATION: synthetic

<400> SEQUENCE: 56
gtcgctgatc aa                                                          12

<210> SEQ ID NO 57
<211> LENGTH: 12
<212> TYPE: DNA
<213> ORGANISM: Artificial Sequence
<220> FEATURE:
<223> OTHER INFORMATION: synthetic

<400> SEQUENCE: 57
tcaactgatc gg                                                          12

<210> SEQ ID NO 58
<211> LENGTH: 12
<212> TYPE: DNA
<213> ORGANISM: Artificial Sequence
<220> FEATURE:
<223> OTHER INFORMATION: synthetic

<400> SEQUENCE: 58
ccagtttcta cg                                                          12

<210> SEQ ID NO 59
<211> LENGTH: 12
<212> TYPE: DNA
<213> ORGANISM: Artificial Sequence
<220> FEATURE:
<223> OTHER INFORMATION: synthetic

<400> SEQUENCE: 59
acccattgcg at                                                              12

<210> SEQ ID NO 60
<211> LENGTH: 12
<212> TYPE: DNA
<213> ORGANISM: Artificial Sequence
<220> FEATURE:
<223> OTHER INFORMATION: synthetic

<400> SEQUENCE: 60
tcaccaccct at                                                              12

<210> SEQ ID NO 61
<211> LENGTH: 12
<212> TYPE: DNA
<213> ORGANISM: Artificial Sequence
<220> FEATURE:
<223> OTHER INFORMATION: synthetic

<400> SEQUENCE: 61
ggtcttcact tc                                                              12

<210> SEQ ID NO 62
<211> LENGTH: 12
<212> TYPE: DNA
<213> ORGANISM: Artificial Sequence
<220> FEATURE:
<223> OTHER INFORMATION: synthetic

<400> SEQUENCE: 62
gttagagatg gg                                                              12

<210> SEQ ID NO 63
<211> LENGTH: 12
<212> TYPE: DNA
<213> ORGANISM: Artificial Sequence
<220> FEATURE:
<223> OTHER INFORMATION: synthetic

<400> SEQUENCE: 63
tcttgcacac tc                                                              12

<210> SEQ ID NO 64
<211> LENGTH: 12
<212> TYPE: DNA
<213> ORGANISM: Artificial Sequence
<220> FEATURE:
<223> OTHER INFORMATION: synthetic

<400> SEQUENCE: 64
ttttctctgc gg                                                              12

<210> SEQ ID NO 65
<211> LENGTH: 12
<212> TYPE: DNA
<213> ORGANISM: Artificial Sequence
<220> FEATURE:
<223> OTHER INFORMATION: synthetic

<400> SEQUENCE: 65
tcagccgagt ta                                                              12

<210> SEQ ID NO 66

```
<211> LENGTH: 12
<212> TYPE: DNA
<213> ORGANISM: Artificial Sequence
<220> FEATURE:
<223> OTHER INFORMATION: synthetic

<400> SEQUENCE: 66
ctcgtgatca ga                                                           12

<210> SEQ ID NO 67
<211> LENGTH: 12
<212> TYPE: DNA
<213> ORGANISM: Artificial Sequence
<220> FEATURE:
<223> OTHER INFORMATION: synthetic

<400> SEQUENCE: 67
cctttctcgg aa                                                           12

<210> SEQ ID NO 68
<211> LENGTH: 12
<212> TYPE: DNA
<213> ORGANISM: Artificial Sequence
<220> FEATURE:
<223> OTHER INFORMATION: synthetic

<400> SEQUENCE: 68
acgctagagc tt                                                           12

<210> SEQ ID NO 69
<211> LENGTH: 12
<212> TYPE: DNA
<213> ORGANISM: Artificial Sequence
<220> FEATURE:
<223> OTHER INFORMATION: synthetic

<400> SEQUENCE: 69
ttccccgttt ag                                                           12

<210> SEQ ID NO 70
<211> LENGTH: 12
<212> TYPE: DNA
<213> ORGANISM: Artificial Sequence
<220> FEATURE:
<223> OTHER INFORMATION: synthetic

<400> SEQUENCE: 70
agaatcgcaa cc                                                           12

<210> SEQ ID NO 71
<211> LENGTH: 12
<212> TYPE: DNA
<213> ORGANISM: Artificial Sequence
<220> FEATURE:
<223> OTHER INFORMATION: synthetic

<400> SEQUENCE: 71
ggaaggaact gt                                                           12

<210> SEQ ID NO 72
<211> LENGTH: 12
<212> TYPE: DNA
<213> ORGANISM: Artificial Sequence
<220> FEATURE:
<223> OTHER INFORMATION: synthetic

<400> SEQUENCE: 72
```
cttggcatct tc					12

<210> SEQ ID NO 73
<211> LENGTH: 12
<212> TYPE: DNA
<213> ORGANISM: Artificial Sequence
<220> FEATURE:
<223> OTHER INFORMATION: synthetic

<400> SEQUENCE: 73
aggccgattt gt					12

<210> SEQ ID NO 74
<211> LENGTH: 12
<212> TYPE: DNA
<213> ORGANISM: Artificial Sequence
<220> FEATURE:
<223> OTHER INFORMATION: synthetic

<400> SEQUENCE: 74
aacaaagggt cc					12

<210> SEQ ID NO 75
<211> LENGTH: 12
<212> TYPE: DNA
<213> ORGANISM: Artificial Sequence
<220> FEATURE:
<223> OTHER INFORMATION: synthetic

<400> SEQUENCE: 75
caattggtag cc					12

<210> SEQ ID NO 76
<211> LENGTH: 12
<212> TYPE: DNA
<213> ORGANISM: Artificial Sequence
<220> FEATURE:
<223> OTHER INFORMATION: synthetic

<400> SEQUENCE: 76
accatcgact ca					12

<210> SEQ ID NO 77
<211> LENGTH: 12
<212> TYPE: DNA
<213> ORGANISM: Artificial Sequence
<220> FEATURE:
<223> OTHER INFORMATION: synthetic

<400> SEQUENCE: 77
cgtgagatga ac					12

<210> SEQ ID NO 78
<211> LENGTH: 12
<212> TYPE: DNA
<213> ORGANISM: Artificial Sequence
<220> FEATURE:
<223> OTHER INFORMATION: synthetic

<400> SEQUENCE: 78
ccatggtctt gt					12

<210> SEQ ID NO 79
<211> LENGTH: 13
<212> TYPE: DNA

```
<213> ORGANISM: Artificial Sequence
<220> FEATURE:
<223> OTHER INFORMATION: synthetic

<400> SEQUENCE: 79
cagatatgag cgc                                                        13

<210> SEQ ID NO 80
<211> LENGTH: 12
<212> TYPE: DNA
<213> ORGANISM: Artificial Sequence
<220> FEATURE:
<223> OTHER INFORMATION: synthetic

<400> SEQUENCE: 80
gtgtgacaga gt                                                         12

<210> SEQ ID NO 81
<211> LENGTH: 12
<212> TYPE: DNA
<213> ORGANISM: Artificial Sequence
<220> FEATURE:
<223> OTHER INFORMATION: synthetic

<400> SEQUENCE: 81
attgtgtgac gg                                                         12

<210> SEQ ID NO 82
<211> LENGTH: 12
<212> TYPE: DNA
<213> ORGANISM: Artificial Sequence
<220> FEATURE:
<223> OTHER INFORMATION: synthetic

<400> SEQUENCE: 82
cggtagtttg ct                                                         12

<210> SEQ ID NO 83
<211> LENGTH: 12
<212> TYPE: DNA
<213> ORGANISM: Artificial Sequence
<220> FEATURE:
<223> OTHER INFORMATION: synthetic

<400> SEQUENCE: 83
ggacatgtcc at                                                         12

<210> SEQ ID NO 84
<211> LENGTH: 12
<212> TYPE: DNA
<213> ORGANISM: Artificial Sequence
<220> FEATURE:
<223> OTHER INFORMATION: synthetic

<400> SEQUENCE: 84
ttgagggaga ca                                                         12

<210> SEQ ID NO 85
<211> LENGTH: 12
<212> TYPE: DNA
<213> ORGANISM: Artificial Sequence
<220> FEATURE:
<223> OTHER INFORMATION: synthetic

<400> SEQUENCE: 85
cgacatcctc ta                                                         12
```

```
<210> SEQ ID NO 86
<211> LENGTH: 12
<212> TYPE: DNA
<213> ORGANISM: Artificial Sequence
<220> FEATURE:
<223> OTHER INFORMATION: synthetic

<400> SEQUENCE: 86
tgagcgagtt ca                                                             12

<210> SEQ ID NO 87
<211> LENGTH: 12
<212> TYPE: DNA
<213> ORGANISM: Artificial Sequence
<220> FEATURE:
<223> OTHER INFORMATION: synthetic

<400> SEQUENCE: 87
gaccttcgga tt                                                             12

<210> SEQ ID NO 88
<211> LENGTH: 12
<212> TYPE: DNA
<213> ORGANISM: Artificial Sequence
<220> FEATURE:
<223> OTHER INFORMATION: synthetic

<400> SEQUENCE: 88
tgtagatccg ca                                                             12

<210> SEQ ID NO 89
<211> LENGTH: 12
<212> TYPE: DNA
<213> ORGANISM: Artificial Sequence
<220> FEATURE:
<223> OTHER INFORMATION: synthetic

<400> SEQUENCE: 89
tggcactcta ga                                                             12

<210> SEQ ID NO 90
<211> LENGTH: 12
<212> TYPE: DNA
<213> ORGANISM: Artificial Sequence
<220> FEATURE:
<223> OTHER INFORMATION: synthetic

<400> SEQUENCE: 90
aacagtagtc gg                                                             12

<210> SEQ ID NO 91
<211> LENGTH: 12
<212> TYPE: DNA
<213> ORGANISM: Artificial Sequence
<220> FEATURE:
<223> OTHER INFORMATION: synthetic

<400> SEQUENCE: 91
tcatgcggaa ag                                                             12

<210> SEQ ID NO 92
<211> LENGTH: 12
<212> TYPE: DNA
<213> ORGANISM: Artificial Sequence
<220> FEATURE:
```

```
<223> OTHER INFORMATION: synthetic

<400> SEQUENCE: 92
tcgaatcgtg tc                                                           12

<210> SEQ ID NO 93
<211> LENGTH: 12
<212> TYPE: DNA
<213> ORGANISM: Artificial Sequence
<220> FEATURE:
<223> OTHER INFORMATION: synthetic

<400> SEQUENCE: 93
ggtgtatagc ca                                                           12

<210> SEQ ID NO 94
<211> LENGTH: 12
<212> TYPE: DNA
<213> ORGANISM: Artificial Sequence
<220> FEATURE:
<223> OTHER INFORMATION: synthetic

<400> SEQUENCE: 94
ttgcagtgca ag                                                           12

<210> SEQ ID NO 95
<211> LENGTH: 12
<212> TYPE: DNA
<213> ORGANISM: Artificial Sequence
<220> FEATURE:
<223> OTHER INFORMATION: synthetic

<400> SEQUENCE: 95
cgattgcaga ag                                                           12

<210> SEQ ID NO 96
<211> LENGTH: 12
<212> TYPE: DNA
<213> ORGANISM: Artificial Sequence
<220> FEATURE:
<223> OTHER INFORMATION: synthetic

<400> SEQUENCE: 96
ccagacgttg tt                                                           12

<210> SEQ ID NO 97
<211> LENGTH: 12
<212> TYPE: DNA
<213> ORGANISM: Artificial Sequence
<220> FEATURE:
<223> OTHER INFORMATION: synthetic

<400> SEQUENCE: 97
tggtggccat aa                                                           12

<210> SEQ ID NO 98
<211> LENGTH: 12
<212> TYPE: DNA
<213> ORGANISM: Artificial Sequence
<220> FEATURE:
<223> OTHER INFORMATION: synthetic

<400> SEQUENCE: 98
cagagtcaat gg                                                           12
```

```
<210> SEQ ID NO 99
<211> LENGTH: 12
<212> TYPE: DNA
<213> ORGANISM: Artificial Sequence
<220> FEATURE:
<223> OTHER INFORMATION: synthetic

<400> SEQUENCE: 99
cctatcattc cc                                                              12

<210> SEQ ID NO 100
<211> LENGTH: 12
<212> TYPE: DNA
<213> ORGANISM: Artificial Sequence
<220> FEATURE:
<223> OTHER INFORMATION: synthetic

<400> SEQUENCE: 100
gaggtatgac tc                                                              12

<210> SEQ ID NO 101
<211> LENGTH: 12
<212> TYPE: DNA
<213> ORGANISM: Artificial Sequence
<220> FEATURE:
<223> OTHER INFORMATION: synthetic

<400> SEQUENCE: 101
ctaggtcaag tc                                                              12

<210> SEQ ID NO 102
<211> LENGTH: 12
<212> TYPE: DNA
<213> ORGANISM: Artificial Sequence
<220> FEATURE:
<223> OTHER INFORMATION: synthetic

<400> SEQUENCE: 102
actcggcttt ca                                                              12

<210> SEQ ID NO 103
<211> LENGTH: 12
<212> TYPE: DNA
<213> ORGANISM: Artificial Sequence
<220> FEATURE:
<223> OTHER INFORMATION: synthetic

<400> SEQUENCE: 103
ttcacaagcg ga                                                              12

<210> SEQ ID NO 104
<211> LENGTH: 52
<212> TYPE: DNA
<213> ORGANISM: Artificial Sequence
<220> FEATURE:
<223> OTHER INFORMATION: synthetic

<400> SEQUENCE: 104
ccaccgctga gcaataacta gtagtgacag gtcgtagatg agtcaacggc ct                  52

<210> SEQ ID NO 105
<211> LENGTH: 52
<212> TYPE: DNA
<213> ORGANISM: Artificial Sequence
<220> FEATURE:
<223> OTHER INFORMATION: synthetic
```

<400> SEQUENCE: 105
ccaccgctga gcaataacta tctgtgaagt cccgtagatg agtcaacggc ct    52

<210> SEQ ID NO 106
<211> LENGTH: 52
<212> TYPE: DNA
<213> ORGANISM: Artificial Sequence
<220> FEATURE:
<223> OTHER INFORMATION: synthetic

<400> SEQUENCE: 106
ccaccgctga gcaataacta atcagatcgc ctcgtagatg agtcaacggc ct    52

<210> SEQ ID NO 107
<211> LENGTH: 52
<212> TYPE: DNA
<213> ORGANISM: Artificial Sequence
<220> FEATURE:
<223> OTHER INFORMATION: synthetic

<400> SEQUENCE: 107
ccaccgctga gcaataacta aatgtggtct cgcgtagatg agtcaacggc ct    52

<210> SEQ ID NO 108
<211> LENGTH: 52
<212> TYPE: DNA
<213> ORGANISM: Artificial Sequence
<220> FEATURE:
<223> OTHER INFORMATION: synthetic

<400> SEQUENCE: 108
ccaccgctga gcaataacta cctctccaaa cacgtagatg agtcaacggc ct    52

<210> SEQ ID NO 109
<211> LENGTH: 52
<212> TYPE: DNA
<213> ORGANISM: Artificial Sequence
<220> FEATURE:
<223> OTHER INFORMATION: synthetic

<400> SEQUENCE: 109
ccaccgctga gcaataacta tactggacaa ggcgtagatg agtcaacggc ct    52

<210> SEQ ID NO 110
<211> LENGTH: 52
<212> TYPE: DNA
<213> ORGANISM: Artificial Sequence
<220> FEATURE:
<223> OTHER INFORMATION: synthetic

<400> SEQUENCE: 110
ccaccgctga gcaataacta tatcggagtc ctcgtagatg agtcaacggc ct    52

<210> SEQ ID NO 111
<211> LENGTH: 52
<212> TYPE: DNA
<213> ORGANISM: Artificial Sequence
<220> FEATURE:
<223> OTHER INFORMATION: synthetic

<400> SEQUENCE: 111
ccaccgctga gcaataacta ggtggagtta ctcgtagatg agtcaacggc ct    52

<210> SEQ ID NO 112
<211> LENGTH: 52

```
<212> TYPE: DNA
<213> ORGANISM: Artificial Sequence
<220> FEATURE:
<223> OTHER INFORMATION: synthetic

<400> SEQUENCE: 112
ccaccgctga gcaataacta cggctactat tgcgtagatg agtcaacggc ct            52

<210> SEQ ID NO 113
<211> LENGTH: 52
<212> TYPE: DNA
<213> ORGANISM: Artificial Sequence
<220> FEATURE:
<223> OTHER INFORMATION: synthetic

<400> SEQUENCE: 113
ccaccgctga gcaataacta ccgagctatg tacgtagatg agtcaacggc ct            52

<210> SEQ ID NO 114
<211> LENGTH: 52
<212> TYPE: DNA
<213> ORGANISM: Artificial Sequence
<220> FEATURE:
<223> OTHER INFORMATION: synthetic

<400> SEQUENCE: 114
ccaccgctga gcaataacta actacgtcca accgtagatg agtcaacggc ct            52

<210> SEQ ID NO 115
<211> LENGTH: 52
<212> TYPE: DNA
<213> ORGANISM: Artificial Sequence
<220> FEATURE:
<223> OTHER INFORMATION: synthetic

<400> SEQUENCE: 115
ccaccgctga gcaataacta ttcatccgaa cgcgtagatg agtcaacggc ct            52

<210> SEQ ID NO 116
<211> LENGTH: 52
<212> TYPE: DNA
<213> ORGANISM: Artificial Sequence
<220> FEATURE:
<223> OTHER INFORMATION: synthetic

<400> SEQUENCE: 116
ccaccgctga gcaataacta cgaaacgctt agcgtagatg agtcaacggc ct            52

<210> SEQ ID NO 117
<211> LENGTH: 52
<212> TYPE: DNA
<213> ORGANISM: Artificial Sequence
<220> FEATURE:
<223> OTHER INFORMATION: synthetic

<400> SEQUENCE: 117
ccaccgctga gcaataacta gcctaagttc cacgtagatg agtcaacggc ct            52

<210> SEQ ID NO 118
<211> LENGTH: 52
<212> TYPE: DNA
<213> ORGANISM: Artificial Sequence
<220> FEATURE:
<223> OTHER INFORMATION: synthetic

<400> SEQUENCE: 118
```
ccaccgctga gcaataacta caattcccac gtcgtagatg agtcaacggc ct    52

<210> SEQ ID NO 119
<211> LENGTH: 52
<212> TYPE: DNA
<213> ORGANISM: Artificial Sequence
<220> FEATURE:
<223> OTHER INFORMATION: synthetic

<400> SEQUENCE: 119
ccaccgctga gcaataacta cggtgagaca tacgtagatg agtcaacggc ct    52

<210> SEQ ID NO 120
<211> LENGTH: 52
<212> TYPE: DNA
<213> ORGANISM: Artificial Sequence
<220> FEATURE:
<223> OTHER INFORMATION: synthetic

<400> SEQUENCE: 120
ccaccgctga gcaataacta ctctgaggtt tgcgtagatg agtcaacggc ct    52

<210> SEQ ID NO 121
<211> LENGTH: 52
<212> TYPE: DNA
<213> ORGANISM: Artificial Sequence
<220> FEATURE:
<223> OTHER INFORMATION: synthetic

<400> SEQUENCE: 121
ccaccgctga gcaataacta tactgtcacc cacgtagatg agtcaacggc ct    52

<210> SEQ ID NO 122
<211> LENGTH: 52
<212> TYPE: DNA
<213> ORGANISM: Artificial Sequence
<220> FEATURE:
<223> OTHER INFORMATION: synthetic

<400> SEQUENCE: 122
ccaccgctga gcaataacta caggaggtac atcgtagatg agtcaacggc ct    52

<210> SEQ ID NO 123
<211> LENGTH: 52
<212> TYPE: DNA
<213> ORGANISM: Artificial Sequence
<220> FEATURE:
<223> OTHER INFORMATION: synthetic

<400> SEQUENCE: 123
ccaccgctga gcaataacta cttcctacag cacgtagatg agtcaacggc ct    52

<210> SEQ ID NO 124
<211> LENGTH: 52
<212> TYPE: DNA
<213> ORGANISM: Artificial Sequence
<220> FEATURE:
<223> OTHER INFORMATION: synthetic

<400> SEQUENCE: 124
ccaccgctga gcaataacta tagaaaccga ggcgtagatg agtcaacggc ct    52

<210> SEQ ID NO 125
<211> LENGTH: 52
<212> TYPE: DNA
<213> ORGANISM: Artificial Sequence
<220> FEATURE:
<223> OTHER INFORMATION: synthetic

<400> SEQUENCE: 125
ccaccgctga gcaataacta gaaaagcgta cccgtagatg agtcaacggc ct        52

<210> SEQ ID NO 126
<211> LENGTH: 52
<212> TYPE: DNA
<213> ORGANISM: Artificial Sequence
<220> FEATURE:
<223> OTHER INFORMATION: synthetic

<400> SEQUENCE: 126
ccaccgctga gcaataacta cgctcataac tccgtagatg agtcaacggc ct        52

<210> SEQ ID NO 127
<211> LENGTH: 52
<212> TYPE: DNA
<213> ORGANISM: Artificial Sequence
<220> FEATURE:
<223> OTHER INFORMATION: synthetic

<400> SEQUENCE: 127
ccaccgctga gcaataacta ggcatatacg accgtagatg agtcaacggc ct        52

<210> SEQ ID NO 128
<211> LENGTH: 52
<212> TYPE: DNA
<213> ORGANISM: Artificial Sequence
<220> FEATURE:
<223> OTHER INFORMATION: synthetic

<400> SEQUENCE: 128
ccaccgctga gcaataacta gtgctctatc accgtagatg agtcaacggc ct        52

<210> SEQ ID NO 129
<211> LENGTH: 52
<212> TYPE: DNA
<213> ORGANISM: Artificial Sequence
<220> FEATURE:
<223> OTHER INFORMATION: synthetic

<400> SEQUENCE: 129
ccaccgctga gcaataacta ggagcatttc accgtagatg agtcaacggc ct        52

<210> SEQ ID NO 130
<211> LENGTH: 52
<212> TYPE: DNA
<213> ORGANISM: Artificial Sequence
<220> FEATURE:
<223> OTHER INFORMATION: synthetic

<400> SEQUENCE: 130
ccaccgctga gcaataacta atgggtcttc tgcgtagatg agtcaacggc ct        52

<210> SEQ ID NO 131
<211> LENGTH: 52
<212> TYPE: DNA
<213> ORGANISM: Artificial Sequence
<220> FEATURE:
<223> OTHER INFORMATION: synthetic

<400> SEQUENCE: 131
ccaccgctga gcaataacta aagtccgtga accgtagatg agtcaacggc ct        52

<210> SEQ ID NO 132
<211> LENGTH: 52
<212> TYPE: DNA
<213> ORGANISM: Artificial Sequence
<220> FEATURE:
<223> OTHER INFORMATION: synthetic

<400> SEQUENCE: 132
ccaccgctga gcaataacta tgacatagag ggcgtagatg agtcaacggc ct        52

<210> SEQ ID NO 133
<211> LENGTH: 52
<212> TYPE: DNA
<213> ORGANISM: Artificial Sequence
<220> FEATURE:
<223> OTHER INFORMATION: synthetic

<400> SEQUENCE: 133
ccaccgctga gcaataacta cgtcaatcgt gtcgtagatg agtcaacggc ct        52

<210> SEQ ID NO 134
<211> LENGTH: 52
<212> TYPE: DNA
<213> ORGANISM: Artificial Sequence
<220> FEATURE:
<223> OTHER INFORMATION: synthetic

<400> SEQUENCE: 134
ccaccgctga gcaataacta gttcgaagca accgtagatg agtcaacggc ct        52

<210> SEQ ID NO 135
<211> LENGTH: 52
<212> TYPE: DNA
<213> ORGANISM: Artificial Sequence
<220> FEATURE:
<223> OTHER INFORMATION: synthetic

<400> SEQUENCE: 135
ccaccgctga gcaataacta acccgaattc accgtagatg agtcaacggc ct        52

<210> SEQ ID NO 136
<211> LENGTH: 52
<212> TYPE: DNA
<213> ORGANISM: Artificial Sequence
<220> FEATURE:
<223> OTHER INFORMATION: synthetic

<400> SEQUENCE: 136
ccaccgctga gcaataacta gaggacttca cacgtagatg agtcaacggc ct        52

<210> SEQ ID NO 137
<211> LENGTH: 52
<212> TYPE: DNA
<213> ORGANISM: Artificial Sequence
<220> FEATURE:
<223> OTHER INFORMATION: synthetic

<400> SEQUENCE: 137
ccaccgctga gcaataacta gattccaccg tacgtagatg agtcaacggc ct        52

<210> SEQ ID NO 138
<211> LENGTH: 52
<212> TYPE: DNA
<213> ORGANISM: Artificial Sequence
<220> FEATURE:
<223> OTHER INFORMATION: synthetic

<400> SEQUENCE: 138
ccaccgctga gcaataacta gtattcgcca tgcgtagatg agtcaacggc ct        52

<210> SEQ ID NO 139
<211> LENGTH: 52
<212> TYPE: DNA
<213> ORGANISM: Artificial Sequence
<220> FEATURE:
<223> OTHER INFORMATION: synthetic

<400> SEQUENCE: 139
ccaccgctga gcaataacta gcttgttatc cgcgtagatg agtcaacggc ct        52

<210> SEQ ID NO 140
<211> LENGTH: 52
<212> TYPE: DNA
<213> ORGANISM: Artificial Sequence
<220> FEATURE:
<223> OTHER INFORMATION: synthetic

<400> SEQUENCE: 140
ccaccgctga gcaataacta cgtccaacta tgcgtagatg agtcaacggc ct        52

<210> SEQ ID NO 141
<211> LENGTH: 52
<212> TYPE: DNA
<213> ORGANISM: Artificial Sequence
<220> FEATURE:
<223> OTHER INFORMATION: synthetic

<400> SEQUENCE: 141
ccaccgctga gcaataacta ggtaacagtg accgtagatg agtcaacggc ct        52

<210> SEQ ID NO 142
<211> LENGTH: 52
<212> TYPE: DNA
<213> ORGANISM: Artificial Sequence
<220> FEATURE:
<223> OTHER INFORMATION: synthetic

<400> SEQUENCE: 142
ccaccgctga gcaataacta gcgcaaaaga agcgtagatg agtcaacggc ct        52

<210> SEQ ID NO 143
<211> LENGTH: 52
<212> TYPE: DNA
<213> ORGANISM: Artificial Sequence
<220> FEATURE:
<223> OTHER INFORMATION: synthetic

<400> SEQUENCE: 143
ccaccgctga gcaataacta tgtggttgat cgcgtagatg agtcaacggc ct        52

<210> SEQ ID NO 144
<211> LENGTH: 52
<212> TYPE: DNA
<213> ORGANISM: Artificial Sequence
<220> FEATURE:
<223> OTHER INFORMATION: synthetic

<400> SEQUENCE: 144
ccaccgctga gcaataacta tgtgggattg tgcgtagatg agtcaacggc ct        52

<210> SEQ ID NO 145

```
<211> LENGTH: 52
<212> TYPE: DNA
<213> ORGANISM: Artificial Sequence
<220> FEATURE:
<223> OTHER INFORMATION: synthetic

<400> SEQUENCE: 145
ccaccgctga gcaataacta tgcttcggga tacgtagatg agtcaacggc ct         52

<210> SEQ ID NO 146
<211> LENGTH: 52
<212> TYPE: DNA
<213> ORGANISM: Artificial Sequence
<220> FEATURE:
<223> OTHER INFORMATION: synthetic

<400> SEQUENCE: 146
ccaccgctga gcaataacta gacagctcgt tacgtagatg agtcaacggc ct         52

<210> SEQ ID NO 147
<211> LENGTH: 52
<212> TYPE: DNA
<213> ORGANISM: Artificial Sequence
<220> FEATURE:
<223> OTHER INFORMATION: synthetic

<400> SEQUENCE: 147
ccaccgctga gcaataacta taagaagcgc tccgtagatg agtcaacggc ct         52

<210> SEQ ID NO 148
<211> LENGTH: 52
<212> TYPE: DNA
<213> ORGANISM: Artificial Sequence
<220> FEATURE:
<223> OTHER INFORMATION: synthetic

<400> SEQUENCE: 148
ccaccgctga gcaataacta catacacact cccgtagatg agtcaacggc ct         52

<210> SEQ ID NO 149
<211> LENGTH: 52
<212> TYPE: DNA
<213> ORGANISM: Artificial Sequence
<220> FEATURE:
<223> OTHER INFORMATION: synthetic

<400> SEQUENCE: 149
ccaccgctga gcaataacta tgccgccaaa atcgtagatg agtcaacggc ct         52

<210> SEQ ID NO 150
<211> LENGTH: 52
<212> TYPE: DNA
<213> ORGANISM: Artificial Sequence
<220> FEATURE:
<223> OTHER INFORMATION: synthetic

<400> SEQUENCE: 150
ccaccgctga gcaataacta cggaccttct aacgtagatg agtcaacggc ct         52

<210> SEQ ID NO 151
<211> LENGTH: 52
<212> TYPE: DNA
<213> ORGANISM: Artificial Sequence
<220> FEATURE:
<223> OTHER INFORMATION: synthetic

<400> SEQUENCE: 151
```
ccaccgctga gcaataacta tctcacgtca accgtagatg agtcaacggc ct          52

<210> SEQ ID NO 152
<211> LENGTH: 52
<212> TYPE: DNA
<213> ORGANISM: Artificial Sequence
<220> FEATURE:
<223> OTHER INFORMATION: synthetic

<400> SEQUENCE: 152
ccaccgctga gcaataacta cgcaagagaa cacgtagatg agtcaacggc ct          52

<210> SEQ ID NO 153
<211> LENGTH: 52
<212> TYPE: DNA
<213> ORGANISM: Artificial Sequence
<220> FEATURE:
<223> OTHER INFORMATION: synthetic

<400> SEQUENCE: 153
ccaccgctga gcaataacta ttagcttccc tgcgtagatg agtcaacggc ct          52

<210> SEQ ID NO 154
<211> LENGTH: 52
<212> TYPE: DNA
<213> ORGANISM: Artificial Sequence
<220> FEATURE:
<223> OTHER INFORMATION: synthetic

<400> SEQUENCE: 154
ccaccgctga gcaataacta gaagccaagc atcgtagatg agtcaacggc ct          52

<210> SEQ ID NO 155
<211> LENGTH: 52
<212> TYPE: DNA
<213> ORGANISM: Artificial Sequence
<220> FEATURE:
<223> OTHER INFORMATION: synthetic

<400> SEQUENCE: 155
ccaccgctga gcaataacta ttcgtagcgt gtcgtagatg agtcaacggc ct          52

<210> SEQ ID NO 156
<211> LENGTH: 52
<212> TYPE: DNA
<213> ORGANISM: Artificial Sequence
<220> FEATURE:
<223> OTHER INFORMATION: synthetic

<400> SEQUENCE: 156
ccaccgctga gcaataacta gtcgctgatc aacgtagatg agtcaacggc ct          52

<210> SEQ ID NO 157
<211> LENGTH: 52
<212> TYPE: DNA
<213> ORGANISM: Artificial Sequence
<220> FEATURE:
<223> OTHER INFORMATION: synthetic

<400> SEQUENCE: 157
ccaccgctga gcaataacta tcaactgatc ggcgtagatg agtcaacggc ct          52

<210> SEQ ID NO 158
<211> LENGTH: 52
<212> TYPE: DNA

```
<213> ORGANISM: Artificial Sequence
<220> FEATURE:
<223> OTHER INFORMATION: synthetic

<400> SEQUENCE: 158
ccaccgctga gcaataacta ccagtttcta cgcgtagatg agtcaacggc ct            52

<210> SEQ ID NO 159
<211> LENGTH: 52
<212> TYPE: DNA
<213> ORGANISM: Artificial Sequence
<220> FEATURE:
<223> OTHER INFORMATION: synthetic

<400> SEQUENCE: 159
ccaccgctga gcaataacta acccattgcg atcgtagatg agtcaacggc ct            52

<210> SEQ ID NO 160
<211> LENGTH: 52
<212> TYPE: DNA
<213> ORGANISM: Artificial Sequence
<220> FEATURE:
<223> OTHER INFORMATION: synthetic

<400> SEQUENCE: 160
ccaccgctga gcaataacta tcaccaccct atcgtagatg agtcaacggc ct            52

<210> SEQ ID NO 161
<211> LENGTH: 52
<212> TYPE: DNA
<213> ORGANISM: Artificial Sequence
<220> FEATURE:
<223> OTHER INFORMATION: synthetic

<400> SEQUENCE: 161
ccaccgctga gcaataacta ggtcttcact tccgtagatg agtcaacggc ct            52

<210> SEQ ID NO 162
<211> LENGTH: 52
<212> TYPE: DNA
<213> ORGANISM: Artificial Sequence
<220> FEATURE:
<223> OTHER INFORMATION: synthetic

<400> SEQUENCE: 162
ccaccgctga gcaataacta gttagagatg ggcgtagatg agtcaacggc ct            52

<210> SEQ ID NO 163
<211> LENGTH: 52
<212> TYPE: DNA
<213> ORGANISM: Artificial Sequence
<220> FEATURE:
<223> OTHER INFORMATION: synthetic

<400> SEQUENCE: 163
ccaccgctga gcaataacta tcttgcacac tccgtagatg agtcaacggc ct            52

<210> SEQ ID NO 164
<211> LENGTH: 52
<212> TYPE: DNA
<213> ORGANISM: Artificial Sequence
<220> FEATURE:
<223> OTHER INFORMATION: synthetic

<400> SEQUENCE: 164
ccaccgctga gcaataacta ttttctctgc ggcgtagatg agtcaacggc ct            52
```

<210> SEQ ID NO 165
<211> LENGTH: 52
<212> TYPE: DNA
<213> ORGANISM: Artificial Sequence
<220> FEATURE:
<223> OTHER INFORMATION: synthetic

<400> SEQUENCE: 165
ccaccgctga gcaataacta tcagccgagt tacgtagatg agtcaacggc ct         52

<210> SEQ ID NO 166
<211> LENGTH: 52
<212> TYPE: DNA
<213> ORGANISM: Artificial Sequence
<220> FEATURE:
<223> OTHER INFORMATION: synthetic

<400> SEQUENCE: 166
ccaccgctga gcaataacta ctcgtgatca gacgtagatg agtcaacggc ct         52

<210> SEQ ID NO 167
<211> LENGTH: 52
<212> TYPE: DNA
<213> ORGANISM: Artificial Sequence
<220> FEATURE:
<223> OTHER INFORMATION: synthetic

<400> SEQUENCE: 167
ccaccgctga gcaataacta cctttctcgg aacgtagatg agtcaacggc ct         52

<210> SEQ ID NO 168
<211> LENGTH: 52
<212> TYPE: DNA
<213> ORGANISM: Artificial Sequence
<220> FEATURE:
<223> OTHER INFORMATION: synthetic

<400> SEQUENCE: 168
ccaccgctga gcaataacta acgctagagc ttcgtagatg agtcaacggc ct         52

<210> SEQ ID NO 169
<211> LENGTH: 52
<212> TYPE: DNA
<213> ORGANISM: Artificial Sequence
<220> FEATURE:
<223> OTHER INFORMATION: synthetic

<400> SEQUENCE: 169
ccaccgctga gcaataacta ttccccgttt agcgtagatg agtcaacggc ct         52

<210> SEQ ID NO 170
<211> LENGTH: 52
<212> TYPE: DNA
<213> ORGANISM: Artificial Sequence
<220> FEATURE:
<223> OTHER INFORMATION: synthetic

<400> SEQUENCE: 170
ccaccgctga gcaataacta agaatcgcaa cccgtagatg agtcaacggc ct         52

<210> SEQ ID NO 171
<211> LENGTH: 52
<212> TYPE: DNA
<213> ORGANISM: Artificial Sequence
<220> FEATURE:

<223> OTHER INFORMATION: synthetic

<400> SEQUENCE: 171
ccaccgctga gcaataacta ggaaggaact gtcgtagatg agtcaacggc ct            52

<210> SEQ ID NO 172
<211> LENGTH: 52
<212> TYPE: DNA
<213> ORGANISM: Artificial Sequence
<220> FEATURE:
<223> OTHER INFORMATION: synthetic

<400> SEQUENCE: 172
ccaccgctga gcaataacta cttggcatct tccgtagatg agtcaacggc ct            52

<210> SEQ ID NO 173
<211> LENGTH: 52
<212> TYPE: DNA
<213> ORGANISM: Artificial Sequence
<220> FEATURE:
<223> OTHER INFORMATION: synthetic

<400> SEQUENCE: 173
ccaccgctga gcaataacta aggccgattt gtcgtagatg agtcaacggc ct            52

<210> SEQ ID NO 174
<211> LENGTH: 52
<212> TYPE: DNA
<213> ORGANISM: Artificial Sequence
<220> FEATURE:
<223> OTHER INFORMATION: synthetic

<400> SEQUENCE: 174
ccaccgctga gcaataacta aacaaagggt cccgtagatg agtcaacggc ct            52

<210> SEQ ID NO 175
<211> LENGTH: 52
<212> TYPE: DNA
<213> ORGANISM: Artificial Sequence
<220> FEATURE:
<223> OTHER INFORMATION: synthetic

<400> SEQUENCE: 175
ccaccgctga gcaataacta caattggtag cccgtagatg agtcaacggc ct            52

<210> SEQ ID NO 176
<211> LENGTH: 52
<212> TYPE: DNA
<213> ORGANISM: Artificial Sequence
<220> FEATURE:
<223> OTHER INFORMATION: synthetic

<400> SEQUENCE: 176
ccaccgctga gcaataacta accatcgact cacgtagatg agtcaacggc ct            52

<210> SEQ ID NO 177
<211> LENGTH: 52
<212> TYPE: DNA
<213> ORGANISM: Artificial Sequence
<220> FEATURE:
<223> OTHER INFORMATION: synthetic

<400> SEQUENCE: 177
ccaccgctga gcaataacta cgtgagatga accgtagatg agtcaacggc ct            52

<210> SEQ ID NO 178
<211> LENGTH: 52
<212> TYPE: DNA
<213> ORGANISM: Artificial Sequence
<220> FEATURE:
<223> OTHER INFORMATION: synthetic

<400> SEQUENCE: 178
ccaccgctga gcaataacta ccatggtctt gtcgtagatg agtcaacggc ct        52

<210> SEQ ID NO 179
<211> LENGTH: 52
<212> TYPE: DNA
<213> ORGANISM: Artificial Sequence
<220> FEATURE:
<223> OTHER INFORMATION: synthetic

<400> SEQUENCE: 179
ccaccgctga gcaataacta agatatgagc gccgtagatg agtcaacggc ct        52

<210> SEQ ID NO 180
<211> LENGTH: 52
<212> TYPE: DNA
<213> ORGANISM: Artificial Sequence
<220> FEATURE:
<223> OTHER INFORMATION: synthetic

<400> SEQUENCE: 180
ccaccgctga gcaataacta gtgtgacaga gtcgtagatg agtcaacggc ct        52

<210> SEQ ID NO 181
<211> LENGTH: 52
<212> TYPE: DNA
<213> ORGANISM: Artificial Sequence
<220> FEATURE:
<223> OTHER INFORMATION: synthetic

<400> SEQUENCE: 181
ccaccgctga gcaataacta attgtgtgac ggcgtagatg agtcaacggc ct        52

<210> SEQ ID NO 182
<211> LENGTH: 52
<212> TYPE: DNA
<213> ORGANISM: Artificial Sequence
<220> FEATURE:
<223> OTHER INFORMATION: synthetic

<400> SEQUENCE: 182
ccaccgctga gcaataacta cggtagtttg ctcgtagatg agtcaacggc ct        52

<210> SEQ ID NO 183
<211> LENGTH: 52
<212> TYPE: DNA
<213> ORGANISM: Artificial Sequence
<220> FEATURE:
<223> OTHER INFORMATION: synthetic

<400> SEQUENCE: 183
ccaccgctga gcaataacta ggacatgtcc atcgtagatg agtcaacggc ct        52

<210> SEQ ID NO 184
<211> LENGTH: 52
<212> TYPE: DNA
<213> ORGANISM: Artificial Sequence
<220> FEATURE:
<223> OTHER INFORMATION: synthetic

<400> SEQUENCE: 184
ccaccgctga gcaataacta ttgagggaga cacgtagatg agtcaacggc ct    52

<210> SEQ ID NO 185
<211> LENGTH: 52
<212> TYPE: DNA
<213> ORGANISM: Artificial Sequence
<220> FEATURE:
<223> OTHER INFORMATION: synthetic

<400> SEQUENCE: 185
ccaccgctga gcaataacta cgacatcctc tacgtagatg agtcaacggc ct    52

<210> SEQ ID NO 186
<211> LENGTH: 52
<212> TYPE: DNA
<213> ORGANISM: Artificial Sequence
<220> FEATURE:
<223> OTHER INFORMATION: synthetic

<400> SEQUENCE: 186
ccaccgctga gcaataacta tgagcgagtt cacgtagatg agtcaacggc ct    52

<210> SEQ ID NO 187
<211> LENGTH: 52
<212> TYPE: DNA
<213> ORGANISM: Artificial Sequence
<220> FEATURE:
<223> OTHER INFORMATION: synthetic

<400> SEQUENCE: 187
ccaccgctga gcaataacta gaccttcgga ttcgtagatg agtcaacggc ct    52

<210> SEQ ID NO 188
<211> LENGTH: 52
<212> TYPE: DNA
<213> ORGANISM: Artificial Sequence
<220> FEATURE:
<223> OTHER INFORMATION: synthetic

<400> SEQUENCE: 188
ccaccgctga gcaataacta tgtagatccg cacgtagatg agtcaacggc ct    52

<210> SEQ ID NO 189
<211> LENGTH: 52
<212> TYPE: DNA
<213> ORGANISM: Artificial Sequence
<220> FEATURE:
<223> OTHER INFORMATION: synthetic

<400> SEQUENCE: 189
ccaccgctga gcaataacta tggcactcta gacgtagatg agtcaacggc ct    52

<210> SEQ ID NO 190
<211> LENGTH: 52
<212> TYPE: DNA
<213> ORGANISM: Artificial Sequence
<220> FEATURE:
<223> OTHER INFORMATION: synthetic

<400> SEQUENCE: 190
ccaccgctga gcaataacta aacagtagtc ggcgtagatg agtcaacggc ct    52

<210> SEQ ID NO 191
<211> LENGTH: 52

<212> TYPE: DNA
<213> ORGANISM: Artificial Sequence
<220> FEATURE:
<223> OTHER INFORMATION: synthetic

<400> SEQUENCE: 191
ccaccgctga gcaataacta tcatgcggaa agcgtagatg agtcaacggc ct        52

<210> SEQ ID NO 192
<211> LENGTH: 52
<212> TYPE: DNA
<213> ORGANISM: Artificial Sequence
<220> FEATURE:
<223> OTHER INFORMATION: synthetic

<400> SEQUENCE: 192
ccaccgctga gcaataacta tcgaatcgtg tccgtagatg agtcaacggc ct        52

<210> SEQ ID NO 193
<211> LENGTH: 52
<212> TYPE: DNA
<213> ORGANISM: Artificial Sequence
<220> FEATURE:
<223> OTHER INFORMATION: synthetic

<400> SEQUENCE: 193
ccaccgctga gcaataacta ggtgtatagc cacgtagatg agtcaacggc ct        52

<210> SEQ ID NO 194
<211> LENGTH: 52
<212> TYPE: DNA
<213> ORGANISM: Artificial Sequence
<220> FEATURE:
<223> OTHER INFORMATION: synthetic

<400> SEQUENCE: 194
ccaccgctga gcaataacta ttgcagtgca agcgtagatg agtcaacggc ct        52

<210> SEQ ID NO 195
<211> LENGTH: 52
<212> TYPE: DNA
<213> ORGANISM: Artificial Sequence
<220> FEATURE:
<223> OTHER INFORMATION: synthetic

<400> SEQUENCE: 195
ccaccgctga gcaataacta cgattgcaga agcgtagatg agtcaacggc ct        52

<210> SEQ ID NO 196
<211> LENGTH: 52
<212> TYPE: DNA
<213> ORGANISM: Artificial Sequence
<220> FEATURE:
<223> OTHER INFORMATION: synthetic

<400> SEQUENCE: 196
ccaccgctga gcaataacta ccagacgttg ttcgtagatg agtcaacggc ct        52

<210> SEQ ID NO 197
<211> LENGTH: 52
<212> TYPE: DNA
<213> ORGANISM: Artificial Sequence
<220> FEATURE:
<223> OTHER INFORMATION: synthetic

<400> SEQUENCE: 197
ccaccgctga gcaataacta tggtggccat aacgtagatg agtcaacggc ct    52

<210> SEQ ID NO 198
<211> LENGTH: 52
<212> TYPE: DNA
<213> ORGANISM: Artificial Sequence
<220> FEATURE:
<223> OTHER INFORMATION: synthetic

<400> SEQUENCE: 198
ccaccgctga gcaataacta cagagtcaat ggcgtagatg agtcaacggc ct    52

<210> SEQ ID NO 199
<211> LENGTH: 52
<212> TYPE: DNA
<213> ORGANISM: Artificial Sequence
<220> FEATURE:
<223> OTHER INFORMATION: synthetic

<400> SEQUENCE: 199
ccaccgctga gcaataacta cctatcattc cccgtagatg agtcaacggc ct    52

<210> SEQ ID NO 200
<211> LENGTH: 52
<212> TYPE: DNA
<213> ORGANISM: Artificial Sequence
<220> FEATURE:
<223> OTHER INFORMATION: synthetic

<400> SEQUENCE: 200
ccaccgctga gcaataacta gaggtatgac tccgtagatg agtcaacggc ct    52

<210> SEQ ID NO 201
<211> LENGTH: 52
<212> TYPE: DNA
<213> ORGANISM: Artificial Sequence
<220> FEATURE:
<223> OTHER INFORMATION: synthetic

<400> SEQUENCE: 201
ccaccgctga gcaataacta ctaggtcaag tccgtagatg agtcaacggc ct    52

<210> SEQ ID NO 202
<211> LENGTH: 52
<212> TYPE: DNA
<213> ORGANISM: Artificial Sequence
<220> FEATURE:
<223> OTHER INFORMATION: synthetic

<400> SEQUENCE: 202
ccaccgctga gcaataacta actcggcttt cacgtagatg agtcaacggc ct    52

<210> SEQ ID NO 203
<211> LENGTH: 52
<212> TYPE: DNA
<213> ORGANISM: Artificial Sequence
<220> FEATURE:
<223> OTHER INFORMATION: synthetic

<400> SEQUENCE: 203
ccaccgctga gcaataacta ttcacaagcg gacgtagatg agtcaacggc ct    52